(12) United States Patent
Inan et al.

(10) Patent No.: US 10,806,374 B2
(45) Date of Patent: Oct. 20, 2020

(54) NONINVASIVE SYSTEMS AND METHODS FOR MONITORING HEALTH CHARACTERISTICS

(71) Applicant: Georgia Tech Research Corporation, Atlanta, GA (US)

(72) Inventors: Omer T. Inan, Atlanta, GA (US); Andrew D. Wiens, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 434 days.

(21) Appl. No.: 15/506,747

(22) PCT Filed: Aug. 25, 2015

(86) PCT No.: PCT/US2015/046829
§ 371 (c)(1),
(2) Date: Feb. 26, 2017

(87) PCT Pub. No.: WO2016/033121
PCT Pub. Date: Mar. 3, 2016

(65) Prior Publication Data
US 2017/0238847 A1    Aug. 24, 2017

Related U.S. Application Data

(60) Provisional application No. 62/041,353, filed on Aug. 25, 2014.

(51) Int. Cl.
*A61B 5/02* (2006.01)
*A61B 5/11* (2006.01)
(Continued)

(52) U.S. Cl.
CPC ............ *A61B 5/1102* (2013.01); *A61B 5/002* (2013.01); *A61B 5/02125* (2013.01);
(Continued)

(58) Field of Classification Search
CPC ... A61B 5/1102; A61B 5/6833; A61B 5/6891; A61B 5/002; A61B 5/6823;
(Continued)

(56) References Cited

U.S. PATENT DOCUMENTS

2007/0152812 A1    7/2007  Wong et al.
2010/0094147 A1    4/2010  Inan et al.
(Continued)

OTHER PUBLICATIONS

International Search Report and Written Opinion for International Patent Application No. PCT/US2015/046829 dated Nov. 13, 2015.

*Primary Examiner* — Navin Natnithithadha
*Assistant Examiner* — Andrey Shostak
(74) *Attorney, Agent, or Firm* — Troutman Pepper Hamilton Sanders LLP; Ryan A. Schneider

(57) ABSTRACT

A wearable system and method for providing BCG data from a user including a wearable sensor configured to receive cardiogenic surface vibration waveforms, a calibrating sensor configured to receive cardiogenic center-of-mass (COM) vibration waveforms, and a processor configured to use the COM vibration waveforms as a template for modifying the surface vibration waveforms to provide health-related outputs. A systematic approach for elucidating the relationship between surface vibrations of the body in the head-to-foot direction from the wearable sensor, and the movements of the whole body as measured by the calibrating sensor is disclosed. Additionally, a methodology for converting the wearable acceleration signals to BCG signals such that the same analysis and interpretation tools can be used for both measurements is presented. High-resolution measurements of the surface accelerations of the body related to the heartbeat with a low weight accelerometer will minimally load the measurement in the transverse direction.

20 Claims, 26 Drawing Sheets
(20 of 26 Drawing Sheet(s) Filed in Color)

(51) Int. Cl.
*A61B 5/021* (2006.01)
*A61B 5/0452* (2006.01)
*A61B 5/00* (2006.01)

(52) U.S. Cl.
CPC .......... *A61B 5/0452* (2013.01); *A61B 5/6823* (2013.01); *A61B 5/6824* (2013.01); *A61B 5/6831* (2013.01); *A61B 5/6833* (2013.01); *A61B 5/6891* (2013.01); *A61B 5/681* (2013.01); *A61B 5/721* (2013.01); *A61B 5/7225* (2013.01); *A61B 2560/0223* (2013.01); *A61B 2562/0219* (2013.01)

(58) Field of Classification Search
CPC ... A61B 5/6824; A61B 5/6831; A61B 5/0452; A61B 5/02125; A61B 5/721; A61B 5/7225; A61B 5/681; A61B 2560/0223; A61B 2562/0219
See application file for complete search history.

(56) References Cited

U.S. PATENT DOCUMENTS

| | | | |
|---|---|---|---|
| 2010/0249633 A1 | 9/2010 | Droitcour et al. | |
| 2011/0021928 A1* | 1/2011 | Giovangrandi | A61B 5/0205 600/484 |
| 2012/0220835 A1* | 8/2012 | Chung | A61B 5/0022 600/301 |
| 2013/0184595 A1* | 7/2013 | Mukkamala | A61B 5/02125 600/485 |
| 2013/0310700 A1* | 11/2013 | Wiard | A61B 5/02125 600/485 |
| 2014/0066798 A1* | 3/2014 | Albert | A61B 5/0452 600/513 |
| 2016/0081563 A1* | 3/2016 | Wiard | A61B 5/0285 600/485 |

* cited by examiner

TABLE I. Results for All Subjects

| Subject | Demographics | | | Sternum | | | PMI | | | Lower Back | | | HR | |
|---|---|---|---|---|---|---|---|---|---|---|---|---|---|---|
| | Gdr. | Ht. (cm) | Wt. (kg) | Age (yrs) | Norm Resid. | Corr. Coef. | No. Beats | Norm Resid. | Corr. Coef. | No. Beats | Norm Resid. | Corr. Coef. | No. Beats | Avg. BPM | σ |
| 1 | M | 178 | 60 | 23 | 1.07 | 0.60 | 88 | 0.94* | 0.76† | 82 | 1.30 | 0.50 | 87 | 72.7 | 5.2 |
| 2 | M | 175 | 69 | 22 | 1.25 | 0.44 | 81 | 1.19* | 0.73† | 78 | 1.55 | 0.72 | 87 | 76.7 | 5.0 |
| 3 | F | 160 | 49 | 22 | 1.08 | 0.67 | 63 | 1.54 | 0.74 | 59 | 1.03* | 0.76† | 73 | 83.6 | 4.7 |
| 4 | M | 185 | 105 | 22 | 0.83 | 0.68 | 77 | 1.01 | 0.85 | 86 | 0.72* | 0.87† | 85 | 90.7 | 3.4 |
| 5 | M | 196 | 98 | 23 | 0.92* | 0.64 | 82 | 1.31 | 0.74 | 63 | 1.24 | 0.78† | 42 | 84.8 | 3.4 |
| 6 | M | 178 | 89 | 32 | 0.86* | 0.76 | 77 | 1.19 | 0.56 | 77 | 0.92 | 0.82† | 77 | 77.9 | 3.0 |
| 7 | M | 185 | 73 | 23 | 0.83 | 0.80 | 101 | 1.08 | 0.74 | 94 | 0.70* | 0.88† | 101 | 72.3 | 3.7 |
| 8 | F | 172 | 52 | 37 | 1.00* | 0.72† | 56 | 1.36 | 0.59 | 59 | 1.13 | 0.70 | 53 | 78.7 | 4.6 |
| 9 | M | 180 | 85 | 26 | 0.57* | 0.91† | 59 | 0.92 | 0.72 | 60 | 0.69 | 0.85 | 65 | 88.1 | 5.7 |
| 10 | F | 165 | 53 | 48 | 0.63* | 0.81† | 23 | 1.44 | 0.69 | 52 | 0.79 | 0.73 | 43 | 100.6 | 5.9 |
| 11 | M | 182 | 85 | 37 | 0.58* | 0.89† | 68 | 1.14 | 0.85 | 70 | 0.98 | 0.78 | 65 | 100.0 | 5.8 |
| 12 | F | 165 | 53 | 22 | 0.77* | 0.84 | 67 | 1.45 | 0.92† | 72 | 1.19 | 0.66 | 69 | 97.8 | 5.3 |
| 13 | F | 160 | 61 | 57 | 1.34 | 0.74† | 63 | 1.23* | 0.40 | 66 | 1.27 | 0.37 | 68 | 97.4 | 4.1 |
| 14 | M | 180 | 78 | 32 | 0.75* | 0.78 | 55 | 1.22 | 0.45 | 63 | 1.04 | 0.87† | 65 | 90.6 | 4.6 |
| 15 | M | 173 | 68 | 24 | 0.51* | 0.91† | 85 | 0.87 | 0.74 | 78 | 1.20 | 0.82 | 81 | 87.4 | 4.3 |
| Avg. | - | 175.6 | 71.9 | 30 | 0.87* | 0.75† | 69.7 | 1.19 | 0.7 | 70.6 | 1.05 | 0.74 | 70.7 | 86.6 | 4.6 |
| σ | - | 10.1 | 17.7 | 10.7 | 0.25 | 0.13 | 18.4 | 0.2 | 0.14 | 11.7 | 0.25 | 0.14 | 16.5 | 9.6 | 0.92 |
| Min | - | 160 | 49 | 22 | 0.51 | 0.44 | 23 | 0.87 | 0.4 | 52 | 0.69 | 0.37 | 42 | 72.3 | 3 |
| Max | - | 196 | 105 | 57 | 1.34 | 0.91 | 101 | 1.54 | 0.92 | 94 | 1.55 | 0.88 | 101 | 100.6 | 5.9 |

FIG. 7

TABLE II. Error Metrics For All Subjects

| Subj. & Gdr. | Demographics | | | Sternum | | | PMI | | | Lower Back | | |
|---|---|---|---|---|---|---|---|---|---|---|---|---|
| | Ht. (cm) | Wt. (kg) | Age (yrs) | I-J Err. | R-J Err. | R-I Err. | Avg. Err. | I-J Err. | R-J Err. | R-I Err. | Avg. Err. | I-J Err. | R-J Err. | R-I Err. | Avg. Err. |
| 1 M | 178 | 60 | 23 | 0.14 | 0.02 | 0.07 | 0.08 | 0.05 | 0.02 | 0.04 | 0.04 | 0.10 | 0.02 | 0.08 | 0.07 |
| 2 M | 175 | 69 | 22 | 0.47 | 0.12 | 0.12 | 0.24 | 0.24 | 0.02 | 0.22 | 0.16 | 0.48 | 0.52 | 0.47 | 0.49 |
| 3 F | 160 | 49 | 22 | 0.29 | 0.05 | 0.08 | 0.14 | 0.35 | 0.09 | 0.15 | 0.2 | 0.35 | 0.08 | 0.13 | 0.19 |
| 4 M | 185 | 105 | 22 | 0.26 | 0.02 | 0.05 | 0.11 | 0.34 | 0.03 | 0.04 | 0.13 | 0.16 | 0.02 | 0.04 | 0.07 |
| 5 M | 196 | 98 | 23 | 0.15 | 0.02 | 0.09 | 0.09 | 0.25 | 0.02 | 0.09 | 0.12 | 0.26 | 0.02 | 0.07 | 0.12 |
| 6 M | 178 | 89 | 32 | 0.06 | 0.01 | 0.07 | 0.05 | 0.05 | 0.004 | 0.02 | 0.02 | 0.11 | 0.01 | 0.03 | 0.05 |
| 7 M | 185 | 73 | 23 | 0.12 | 0.01 | 0.02 | 0.05 | 0.13 | 0.02 | 0.06 | 0.07 | 0.19 | 0.03 | 0.05 | 0.09 |
| 8 F | 172 | 52 | 37 | 0.33 | 0.14 | 0.22 | 0.23 | 0.22 | 0.02 | 0.04 | 0.09 | 0.10 | 0.00 3 | 0.03 | 0.04 |
| 9 M | 180 | 85 | 26 | 0.11 | 0.01 | 0.05 | 0.06 | 0.09 | 0.03 | 0.07 | 0.06 | 0.20 | 0.01 | 0.01 | 0.07 |
| 10 F | 165 | 53 | 48 | 0.56 | 0.04 | 0.11 | 0.24 | 0.35 | 0.03 | 0.14 | 0.17 | 0.46 | 0.08 | 0.08 | 0.21 |
| 11 M | 182 | 85 | 37 | 0.13 | 0.01 | 0.02 | 0.05 | 0.27 | 0.01 | 0.02 | 0.10 | 0.04 | 0.01 | 0.01 | 0.02 |
| 12 F | 165 | 53 | 22 | 0.30 | 0.01 | 0.12 | 0.14 | 0.15 | 0.02 | 0.04 | 0.07 | 0.22 | 0.01 | 0.03 | 0.09 |
| 13 F | 160 | 61 | 57 | 0.20 | 0.20 | 0.28 | 0.23 | 0.45 | 0.29 | 0.42 | 0.39 | 0.23 | 0.02 | 0.03 | 0.09 |
| 14 M | 180 | 78 | 32 | 0.34 | 0.14 | 0.23 | 0.24 | 0.07 | 0.04 | 0.05 | 0.05 | 0.14 | 0.01 | 0.04 | 0.06 |
| 15 M | 173 | 68 | 24 | 0.29 | 0.02 | 0.05 | 0.12 | 0.19 | 0.06 | 0.08 | 0.11 | 0.25 | 0.03 | 0.05 | 0.11 |
| Avg. | 176 | 71.9 | 30 | 0.25 | 0.05 | 0.10 | 0.14 | 0.21* | 0.05* | 0.10 | 0.12 | 0.22 | 0.06 | 0.08* | 0.12* |
| Min. | 160 | 49 | 22 | 0.06 | 0.01 | 0.02 | 0.05 | 0.05 | 0.00 | 0.02 | 0.02 | 0.04 | 0.00 | 0.01 | 0.02 |
| Max. | 196 | 105 | 57 | 0.56 | 0.2 | 0.28 | 0.24 | 0.45 | 0.29 | 0.42 | 0.39 | 0.48 | 0.52 | 0.47 | 0.49 |
| Med. | 178 | 69 | 24 | 0.26 | 0.02 | 0.08 | 0.12 | 0.22 | 0.02 | 0.06 | 0.10 | 0.20 | 0.02 | 0.04 | 0.09 |
| σ | 10.1 | 17.7 | 10.7 | 0.14 | 0.06 | 0.08 | 0.08 | 0.12 | 0.07 | 0.10 | 0.09 | 0.13 | 0.13 | 0.11 | 0.11 |

The best location is marked with an asterisk (*).

FIG. 12

NONINVASIVE SYSTEMS AND METHODS FOR MONITORING HEALTH CHARACTERISTICS

CROSS-REFERENCE TO RELATED APPLICATIONS

This application claims the benefit of U.S. Provisional Application No. 62/041,353 filed 25 Aug. 2014 the entire contents and substance of which is hereby incorporated by reference.

BACKGROUND OF THE INVENTION

1. Field of the Invention

The present invention relates generally to noninvasive systems and methods for monitoring health characteristics, and more specifically to noninvasive systems and methods for monitoring heart health characteristics with a wearable ballistocardiogram (BCG).

2. Description of Related Art

Cardiovascular disease (CVD) represents one of the biggest challenges facing society today and in the coming decades. In 2013, CVD accounted for one in four deaths in the US, and afflicted more than 1 in 3 people; by 2030, the American Heart Association (AHA) projects that 40.5% of Americans will suffer with CVD and the projected medical costs will exceed $800 billion. 47% of sudden cardiac deaths occur outside of the hospital. At the same time, in the coming years, there is a projected shortage in the number of healthcare providers both in the US and worldwide. The combination of increasing numbers of patients with CVD, increasing medical costs related to CVD, and decreasing number of providers can only be addressed by dramatic changes in the way that care is delivered.

Continuous heart monitoring has the potential to not only reduce costs associated with invasive and minimally invasive testing but also to improve the quality of life for many who are struggling with CVD and to provide the capability of early detection and preventative care.

Home monitoring of cardiovascular health represents a viable alternative to the current model of proactive CVD management. Actionable solutions for physiological monitoring at home that capture the complexity required for titrating care could greatly reduce healthcare costs, improve the effectiveness of the therapy by better addressing the changing needs of the patients, and empower the patients against their diseases by enabling them with information regarding their physiological state. Successful home monitoring technologies must be unobtrusive, inexpensive, accurate, and robust, and importantly must provide sufficiently comprehensive information about the person's health such that therapies can be adjusted based on valid physiological relationships.

In terms of monitoring CVD at home, such a comprehensive assessment would require information regarding both the electrical and mechanical aspects of cardiovascular function. However, conventional technologies for unobtrusively assessing the mechanical aspects are greatly limited, and in general not amenable for home use. Ballistocardiography (BCG), the measurement of the mechanical forces of the body in reaction to cardiac ejection of blood, has shown promise in recent studies for offering a possible solution to this technological need.

The BCG phenomenon was first discovered in the 1800s following J. W. Gordon's paper in 1877 explaining how the needle on a weighing scale fluctuates with the rhythm of the heart. Gordon speculated that the cause was ejection of blood into the aorta, comparing the recoil to "a ball propelled from a gun." Studies with human subjects in the mid-20th century led to the discovery that the BCG can be used to detect heart malfunctions.

In an attempt to simplify the instrumentation required for measuring such vibrations of the body in response to the heartbeat, researchers developed another similar technique named seismocardiography (SCG), a measure of local acceleration of the chest wall resulting from the heartbeat. In contrast to BCG, which required elaborate stationary tables and beds, SCG could be measured by simply placing a small accelerometer on the chest of a supine subject. However, as the subsequent revolution in solid-state electronics led to significant progress in electrical heart monitoring techniques, and imaging technologies (ultrasound and magnetic resonance imaging, MRI) became widely prevalent in clinical practice, BCG research reached a nadir in the late 1980s.

Over the past two decades, developments in the semiconductor process have led to extremely low-cost and low-power microelectromechanical systems (MEMS) sensors and microprocessors. These developments promise the ability to more precisely measure and process BCG and SCG signals with relatively small and low-cost equipment in ways that have never before been possible. Simultaneously, the need for inexpensive medical equipment capable of measuring large quantities of physiological parameters outside of clinical settings—such as in the home—is imminent. Interest in BCG is thus returning, and the volume of publications has been trending upward.

BCG and SCG measurements have been demonstrated using stationary objects, for example, beds, chairs, and modified home weighing scales. BCG stationary systems provide measurements that correlate strongly to changes in cardiac output, contractility, and beat-by-beat left ventricular function—all three of these representing central aspects of mechanical function.

While these platforms are relatively well understood, they do not offer mobility, nor the ability to monitor cardiac function continuously throughout the day. Continuous measurement of BCG signals using a wearable device greatly enhances the capabilities of techniques for assessing cardiovascular health at home. If BCG signals were continuously obtained throughout the day and night, then specific responses of cardiac output and contractility to perturbations such as ambient temperature, posture, activity, and sleep could be gathered, and a more comprehensive picture of the person's cardiovascular health could be obtained.

Accordingly, researchers have developed wearable systems based on miniature accelerometers in attempts to measure BCG signals continuously. However, since the morphology and timing of the signals from wearable systems are significantly different from BCG signals measured using the weighing scale or other historical techniques such as the Starr Table, the analysis and interpretation techniques developed for BCG signals cannot directly be applied to these wearable acceleration measurements.

Simply put, wearable accelerometers produce signals that are fundamentally different from both the conventional BCG and SCG: while the BCG represents movements of the whole body, and the SCG represents accelerations of the chest wall, the wearable BCG represents accelerations of the surface of the skin at an arbitrary location on the body. Thus, simply interpreting the wearable BCG signal as a displacement BCG yields incorrect cardiac assessments.

For example, while the time interval between the electrocardiogram (ECG) R-wave peak and the BCG J-wave peak—the R-J interval—has been found to be typically 250 ms for a healthy adult measured with the well understood and studied static-charge-sensitive bed apparatus, and ranged from 203-290 ms for 92 healthy subjects participating in a study with the well understood weighing scale system, for the accelerometer-based wearable system, the R-J interval was found to be between 150-180 ms. These differences are profound and evidence that interpreting the wearable BCG signal as a displacement BCG yields incorrect cardiac assessments.

In another study, an accelerometer-based BCG system produced an R-J interval of 133 ms, evidencing even further discrepancies with the known 203-290 ms from well studied systems.

Cardiac timing measurements such as the R-J interval are clinically important for a number of reasons. Calcium ions regulate contractility and relaxation of the heart, and recycling of these ions controls the timing of cardiac events. Regulation of calcium ions is thus critically important in mechanical dysfunction and arrhythmia. Since cardiac timing exhibits millisecond precision, it is a good measure of myocardial cellular health, and irregularities in timing measurements are generally the first indication of problems in cardiac performance.

It is thus an intention of the present invention to investigate how surface vibrations (for example, from a wearable system) compare to whole body vibrations (for example, from stationary BCG/SCG systems), and confirm that the same analysis techniques and human subject findings cannot be applied to both of these signals. This analysis begins with an investigation into the significant differences in signal morphology between wearable and stationary BCG measurements, thus providing insights into the differences in wearable measurements depending on a number of factors, including location on the body where they are taken. The present invention ultimately examines methodologies for converting the wearable acceleration signals to BCG signals such that, indeed, similar if not the same analysis and interpretation tools can be used for both measurements.

BRIEF SUMMARY OF THE INVENTION

Briefly described, in a preferred form, the present invention comprises systems and methods for measuring a central, mechanical, cardiovascular event—the ejection of blood from the heart into the aorta—from a distal location, for example, the wrist, in such a way that continuous/long-term recordings, for example throughout the day, can be obtained. The present technical advances provide all of the information that conventional approaches provide (i.e. heart rate), and additional provide information on the mechanical forces of the heart, which is described herein to be related to clinically relevant parameters of health (e.g. cardiac output). Furthermore, the measurement can be paired together with one or more cardiovascular measurements (such as optical sensing of blood flow to the wrist) and calculate pulse transit time that has been shown to be inversely correlated to blood pressure.

The present invention builds upon key findings to present a system and method for providing BCG data from a user comprising a wearable sensor configured to receive cardiogenic surface vibration waveforms, a calibrating sensor configured to receive cardiogenic center-of-mass (COM) vibration waveforms, and a processor configured to use the COM vibration waveforms as a template for modifying the surface vibration waveforms to provide health-related outputs.

While the BCG is fundamentally a measure of the hemodynamics, wearable BCG measurements can also include other phenomena, such as the heart sounds and the movement of the heart itself. The present invention provides a better understanding and quantifying of the relationship between cardiogenic forces measured from the calibrating sensor (the whole body) compared to locally interrogated representations from the wearable sensor.

Key findings leading to many of the innovative technical contributions of the present invention include:

that acceleration waveforms in the head-to-foot direction measured on the user's body by the wearable sensor more closely resemble the second derivative of the BCG measured by the calibrating sensor (for example, a weighing scale), not the BCG signal itself measured by the calibrating sensor;

that acceleration signals in the head-to-foot direction measured from the chest on the user's body by the wearable sensor cannot always be directly transformed into displacement BCG signals using double integration in time; and for a small population of users, the position of the wearable sensor on the user's body providing the closest match to the second derivative of the BCG was user-dependent.

The present invention further comprises a systematic approach for elucidating the relationship between surface vibrations of the body in the head-to-foot direction from the wearable sensor, and the movements of the whole body as measured by the calibrating sensor. Additionally, a methodology for converting the wearable acceleration signals to BCG signals such that the same analysis and interpretation tools can be used for both measurements is presented. The present invention provides the first high-resolution (low electronic noise) measurements of the surface accelerations of the body related to the heartbeat with a low weight accelerometer that will minimally load the measurement in the transverse direction.

The present invention further comprises enabling wearable, and thus continuous, recording of BCG signals that greatly expand the capabilities of the technique; however, BCG signals measured using wearable devices are morphologically dissimilar to measurements from "fixed" instruments, precluding the analysis and interpretation techniques from one domain to be applied to the other. In particular, the time intervals between the ECG and BCG—namely, the R-J interval, a surrogate for measuring contractility changes—are significantly different for the accelerometer compared to a "fixed" BCG measurement. The present invention provides for quantitatively normalizing wearable BCG measurement to "fixed" measurements with a systematic experimental approach. With these methods, the same analysis and interpretation techniques developed over the past decade for "fixed" BCG measurement can be successfully translated to wearable measurements.

Further, systolic time intervals (STI) are non-invasive measures of cardiac function. Due to the fact that STI can be measured noninvasively outside the clinic, STI are a promising method for long-term monitoring of patients with CVD. In particular, the pre-ejection period (PEP) has been measured successfully from body vibrations of the beating heart, BCG, using a weighing scale. Similar measurements can be made with on-body accelerometers, however these wearable BCG signals are typically more challenging to interpret than whole-body BCG.

In another exemplary embodiment of the present invention, a small pilot study with four subjects was used to investigate whether a body sensor network of four accelerometers positioned on the wrist, arm, sternum, and head could improve beat-by-beat PEP prediction beyond that of each sensor alone. Linear models were fitted from the R-J and R-I intervals of the four BCG signals to PEP measured with impedance cardiography from five minute recordings after isometric lower-body exercise. Specifically, it was found that (i) the root mean square error (RMSE) of PEP estimation from the wearable BCG sensors can be reduced by using double integration, (ii) the standard deviation of PEP estimates from R-I intervals was smaller than from R-J intervals, and (iii) linear models combining both R-J and R-I measurements from all sensors resulted in the best average correlation ($r^2=0.96\pm0.01$) and lowest average RMSE ($2.5\pm0.8$ ms) from 5×2-fold cross validation.

The present invention is capable of removing conventional issues with wearable sensors, minimizing if not eliminating concerns like the non-repeatability of a user placing the wearable sensor in the exact same location on the body time and again, or in the same orientation, or other normal user day-to-day issues when removing and then placing once again, a wearable sensor upon the body (like a watch, or patch, or other item that will likely have a different orientation, location, or other changed condition each time it is worn).

In another exemplary embodiment, the present invention comprises innovative measurement systems for measurement of surface vibrations. An accelerometer-based surface vibration measurement can be made from various locations including the wrist, sternum, lower back and behind the ear. An accelerometer-based measurement can be made inside the body by a pacemaker. Optical methods of surface vibration measurements are disclosed. The present invention further comprises measurement of surface vibrations from a handheld device, mechanical methods, inertial sensors and RF measurement.

In another exemplary embodiment, the present invention comprises measurement systems for measurement of COM vibration waveform measurement techniques. For example, beds with local cells, instrumented mattresses or pillows, or with charge sensitive films capable of measuring the movement of whole body in response to the heartbeat are discloses. Chairs with piezoelectric film, load cells or other sensors can be used to measure the COM BCG. Further, shoes with integrated sensors (pressure sensors) can be used to measure COM BCG.

In another exemplary embodiment, the present invention comprises various algorithms for performing the modification of the surface vibration signal using system identification techniques such as adaptive filters and non-linear methods. Health metrics can include changes in the contractile properties of the heart using variations in the time interval between R-wave and J-wave.

In another exemplary embodiment, the present invention further modifies inventive double integration filtering by training the filter using systolic time intervals extracted from an impedance cardiogram.

In another exemplary embodiment, the invention does not require estimating whole-body BCG in order to provide its beneficial results. Accuracy can be improved by going directly from local surface vibration measurements to cardiac timing. The present invention enables the combination of measurements from sensors placed on more than one location on the body.

These and other objects, features and advantages of the present invention will become more apparent upon reading the following specification in conjunction with the accompanying drawing figures.

BRIEF DESCRIPTION OF THE DRAWINGS

The patent or application file contains at least one drawing executed in color. Copies of this patent or patent application publication with color drawings will be provided by the Office Upon request and payment of the necessary fee.

FIG. 7 is TABLE I, showing the normalized residual and correlation coefficient values for all subjects for the positions investigated in FIG. 6.

FIG. 12 is TABLE II, showing the error metrics for all subjects of FIG. 7, TABLE I.

DETAIL DESCRIPTION OF THE INVENTION

Figure 1:
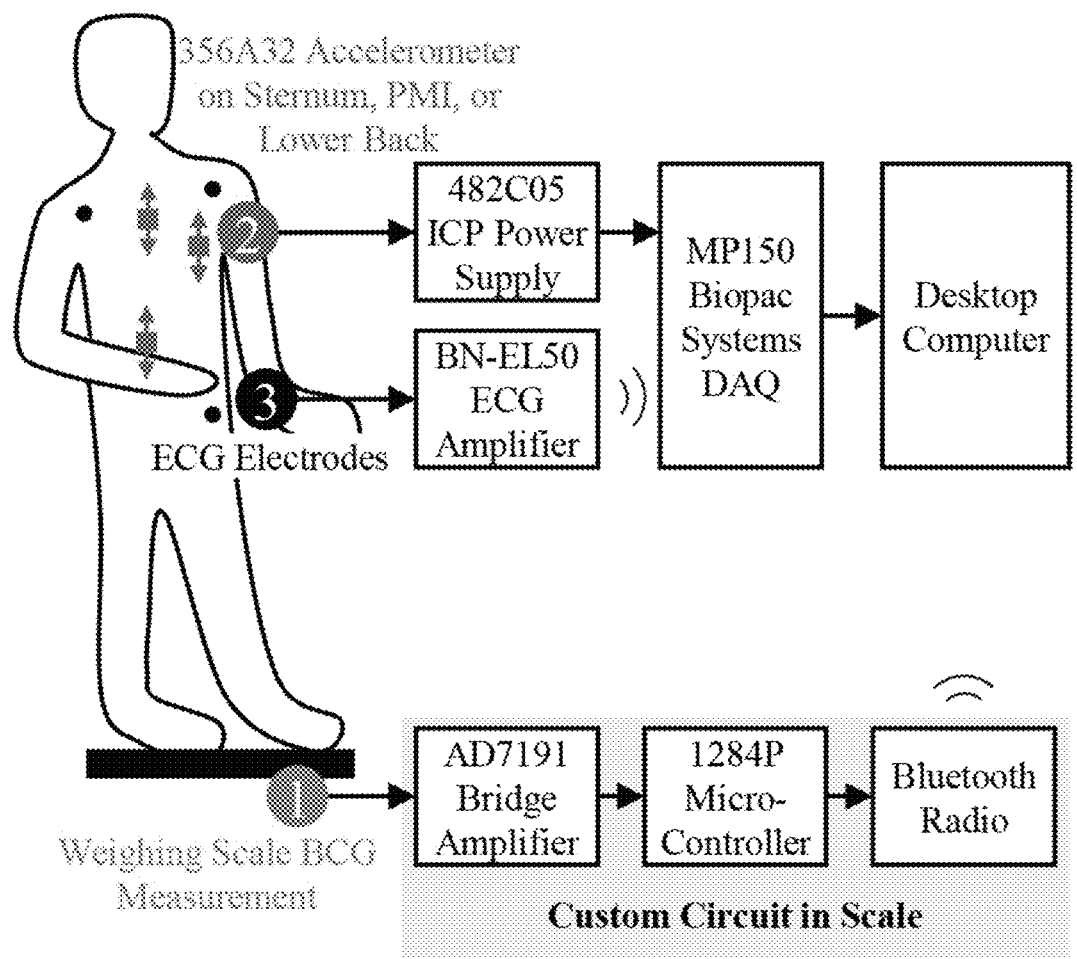
FIG. 1 is a block diagram of measurement setup according to an exemplary embodiment of the present invention, showing three main accelerometer placement locations analyzed.

To facilitate an understanding of the principles and features of the various embodiments of the invention, various illustrative embodiments are explained below. Although exemplary embodiments of the invention are explained in detail, it is to be understood that other embodiments are contemplated. Accordingly, it is not intended that the invention is limited in its scope to the details of construction and arrangement of components set forth in the following description or illustrated in the drawings. The invention is capable of other embodiments and of being practiced or carried out in various ways. Also, in describing the exemplary embodiments, specific terminology will be resorted to for the sake of clarity.

It must also be noted that, as used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named.

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value.

Similarly, as used herein, "substantially free" of something, or "substantially pure", and like characterizations, can include both being "at least substantially free" of something, or "at least substantially pure", and being "completely free" of something, or "completely pure".

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

The materials described as making up the various elements of the invention are intended to be illustrative and not restrictive. Many suitable materials that would perform the same or a similar function as the materials described herein are intended to be embraced within the scope of the invention. Such other materials not described herein can include, but are not limited to, for example, materials that are developed after the time of the development of the invention.

In some instances, a computing device may be referred to as a mobile device, mobile computing device, a mobile station (MS), terminal, cellular phone, cellular handset, personal digital assistant (PDA), smart phone, wireless phone, organizer, handheld computer, desktop computer, laptop computer, tablet computer, set-top box, television, appliance, game device, medical device, display device, or some other like terminology. In other instances, a computing device may be a processor, controller, or a central processing unit (CPU). In yet other instances, a computing device may be a set of hardware components.

Various aspects described herein may be implemented using standard programming or engineering techniques to produce software, firmware, hardware, or any combination thereof to control a computing device to implement the disclosed subject matter. A computer-readable medium may include, for example: a magnetic storage device such as a hard disk, a floppy disk or a magnetic strip; an optical storage device such as a compact disk (CD) or digital versatile disk (DVD); a smart card; and a flash memory device such as a card, stick or key drive, or embedded component. Additionally, it should be appreciated that a carrier wave may be employed to carry computer-readable electronic data including those used in transmitting and receiving electronic data such as electronic mail (e-mail) or in accessing a computer network such as the Internet or a local area network (LAN). Of course, a person of ordinary skill in the art will recognize many modifications may be made to this configuration without departing from the scope or spirit of the claimed subject matter.

Various systems, methods, and computer-readable mediums may be utilized for gamifying real-time network communications between users and will now be described with reference to the accompanying figures.

It will be understood by those of skill in the art that the present invention may incorporate various types computing device architectures. They may be embodied in a computing device (for example, a dedicated server computer or a mobile computing device). It will be understood that the computing device architecture is provided for example purposes only and does not limit the scope of the various embodiments of the present disclosed systems, methods, and computer-readable mediums.

The computing device architecture can include a CPU, where computer instructions are processed; a display interface that acts as a communication interface and provides functions for rendering video, graphics, images, and texts on the display. According to certain some embodiments of the disclosed technology, the display interface may be directly connected to a local display, such as a touch-screen display associated with a mobile computing device. In another example embodiment, the display interface may be configured for providing data, images, and other information for an external/remote display that is not necessarily physically connected to the mobile computing device. For example, a desktop monitor may be utilized for mirroring graphics and other information that is presented on a mobile computing device. According to certain some embodiments, the display interface may wirelessly communicate, for example, via a Wi-Fi channel or other available network connection interface to the external/remote display.

In an example embodiment, the network connection interface may be configured as a communication interface and may provide functions for rendering video, graphics, images, text, other information, or any combination thereof on the display. In one example, a communication interface may include a serial port, a parallel port, a general purpose input and output (GPIO) port, a game port, a universal serial bus (USB), a micro-USB port, a high definition multimedia (HDMI) port, a video port, an audio port, a Bluetooth port, a near-field communication (NFC) port, another like communication interface, or any combination thereof.

The computing device architecture may include a keyboard interface that provides a communication interface to a keyboard. The computing device architecture may be configured to use an input device via one or more of input/output interfaces (for example, the keyboard interface, the display interface, the presence sensitive display interface, network connection interface, camera interface, sound interface, etc.) to allow a user to capture information into the computing device architecture. The input device may include a mouse, a trackball, a directional pad, a track pad, a touch-verified track pad, a presence-sensitive track pad, a presence-sensitive display, a scroll wheel, a digital camera, a digital video camera, a web camera, a microphone, a sensor, a smartcard, and the like. Additionally, the input device may be integrated with the computing device architecture or may be a separate device. For example, the input device may be an accelerometer, a magnetometer, a digital camera, a microphone, and an optical sensor.

Example embodiments of the computing device architecture may include an antenna interface that provides a communication interface to an antenna; a network connection interface that provides a communication interface to a network. According to certain embodiments, a camera interface is provided that acts as a communication interface and provides functions for capturing digital images from a camera or other image/video capture device. According to certain embodiments, a sound interface is provided as a communication interface for converting sound into electrical signals using a microphone and for converting electrical signals into sound using a speaker. According to example embodiments, a random access memory (RAM) is provided, where computer instructions and data may be stored in a volatile memory device for processing by the CPU.

According to an example embodiment, the computing device architecture includes a read-only memory (ROM) where invariant low-level system code or data for basic system functions such as basic input and output (I/O), startup, or reception of keystrokes from a keyboard are stored in a non-volatile memory device. According to an example embodiment, the computing device architecture includes a storage medium or other suitable type of memory (e.g., RAM, ROM, programmable read-only memory (PROM), erasable programmable read-only memory (EPROM), electrically erasable programmable read-only memory (EEPROM), magnetic disks, optical disks, floppy disks, hard disks, removable cartridges, flash drives), where the files include an operating system, application programs (including, for example, a web browser application, a widget or gadget engine, and or other applications, as necessary) and data files are stored.

According to an example embodiment, the computing device architecture includes a power source that provides an appropriate alternating current (AC) or direct current (DC)

to power components. According to an example embodiment, the computing device architecture includes a telephony subsystem that allows the device to transmit and receive sound over a telephone network. The constituent devices and the CPU communicate with each other over a bus.

According to an example embodiment, the CPU has appropriate structure to be a computer processor. In one arrangement, the CPU may include more than one processing unit. The RAM interfaces with the computer bus to provide quick RAM storage to the CPU during the execution of software programs such as the operating system application programs, and device drivers. More specifically, the CPU loads computer-executable process steps from the storage medium or other media into a field of the RAM in order to execute software programs. Data may be stored in the RAM, where the data may be accessed by the computer CPU during execution. In one example configuration, the device architecture includes at least 125 MB of RAM, and 256 MB of flash memory.

The storage medium itself may include a number of physical drive units, such as a redundant array of independent disks (RAID), a floppy disk drive, a flash memory, a USB flash drive, an external hard disk drive, thumb drive, pen drive, key drive, a High-Density Digital Versatile Disc (HD-DVD) optical disc drive, an internal hard disk drive, a Blu-Ray optical disc drive, or a Holographic Digital Data Storage (HDDS) optical disc drive, an external mini-dual in-line memory module (DIMM) synchronous dynamic random access memory (SDRAM), or an external micro-DIMM SDRAM. Such computer readable storage media allow a computing device to access computer-executable process steps, application programs and the like, stored on removable and non-removable memory media, to off-load data from the device or to upload data onto the device. A computer program product, such as one utilizing a communication system may be tangibly embodied in storage medium, which may comprise a machine-readable storage medium.

According to one example embodiment, the term computing device, as used herein, may be a CPU, or conceptualized as a CPU (for example, the CPU). In this example embodiment, the computing device may be coupled, connected, or in communication with one or more peripheral devices, such as display, camera, speaker, or microphone.

In some embodiments of the disclosed technology, the computing device may include any number of hardware or software applications that are executed to facilitate any of the operations. In some embodiments, one or more I/O interfaces may facilitate communication between the computing device and one or more input/output devices. For example, a universal serial bus port, a serial port, a disk drive, a CD-ROM drive, or one or more user interface devices, such as a display, keyboard, keypad, mouse, control panel, touch screen display, microphone, etc., may facilitate user interaction with the computing device. The one or more I/O interfaces may be utilized to receive or collect data and/or user instructions from a wide variety of input devices. Received data may be processed by one or more computer processors as desired in various embodiments of the disclosed technology and/or stored in one or more memory devices.

One or more network interfaces may facilitate connection of the computing device inputs and outputs to one or more suitable networks or connections; for example, the connections that facilitate communication with any number of sensors associated with the system. The one or more network interfaces may further facilitate connection to one or more suitable networks; for example, a local area network, a wide area network, the Internet, a cellular network, a radio-frequency network, a Bluetooth-enabled network, a Wi-Fi-enabled network, a satellite-based network, any wired network, any wireless network, etc., for communication with external devices or systems.

In an exemplary embodiment, the present invention comprises a system for providing BCG data from a user comprising a wearable sensor configured to receive, from a user, cardiogenic surface vibration waveforms, a calibrating sensor configured to receive, from the user, cardiogenic center-of-mass (COM) vibration waveforms, and a processor configured to use the COM vibration waveforms as a template for modifying the surface vibration waveforms to provide at least one health-related output.

As discussed, the present invention minimizes if not eliminates human error or simply human action in the periodic removing and replacing a wearable sensor upon the body. For example, a wristwatch might be worn each day, but it cannot have the same tightness, or same orientation, or same location about the wrist/arm each time it is worn. Nor can a wearable sensor in the form of a patch. Even if location can be nearly the same, the rotational orientation of the patch might be difficult for a user to reproduce each time it is placed on the body, even if the patch has indicia to help the user repeatably align the orientation time and again. The present invention overcomes such issues with its innovative approach to calibration.

A health-related output can comprise a condition of the user's heart. A health-related output can comprise systolic time interval measurements. A health-related output can comprise cardiac output or changes in cardiac output.

The wearable sensor can be a wearable wrist sensor. The wearable sensor can comprises an elastic band, such as on the arm or chest. The wearable sensor can comprise an adhesive patch placed on the skin.

The calibrating sensor can comprise a weighing scale configured to measure BCG signals. The calibrating sensor can comprise a chair configured to measure BCG signals. The calibrating sensor can be built into a bed to measure BCG signals.

The processor can be configured to run an algorithm for modifying the surface vibration waveforms using a regularized least squares based system identification method using the COM vibration waveforms as calibration waveforms to modify the surface vibration waveforms.

The processor can be configured to run an algorithm for modifying the surface vibration waveforms using adaptive signal estimation and the calibrating sensor waveform as the desired response.

These innovative approaches are described in detail below.

I. Towards Continuous, Non-Invasive Assessment of Ventricular Function and Hemodynamics: Wearable Ballistocardiography In a first exemplary embodiment of the present invention, a systematic approach for elucidating the relationship between these surface vibrations of the body in the head-to-foot direction, and the movements of the whole body as measured by the BCG-equipped weighing scale is examined. In another exemplary embodiment of the present invention, a methodology for mathematically converting the wearable acceleration signals to BCG signals such that the same analysis and interpretation tools can be used for both measurements is disclosed. In yet another exemplary embodiment of the present invention, high-resolution (low electronic noise) measurements of the surface accelerations of the body related to the heartbeat with a low weight accelerometer that will minimally load the measurement in the transverse direction is disclosed.

Methods and Design Approach

Hardware Design and Data Collection

In one study, a protocol was used, reviewed and approved by the Georgia Institute of Technology (GT) Institutional Review Board (IRB). All subjects provided written informed consent before experimentation. Fifteen healthy subjects were recruited for this study, including ten men and five women with ages ranging from 22 to 57. Similar to other studies in the existing literature, each subject served as his or her own control since relationships between measurements made on the same individuals were examined.

Figure 2:
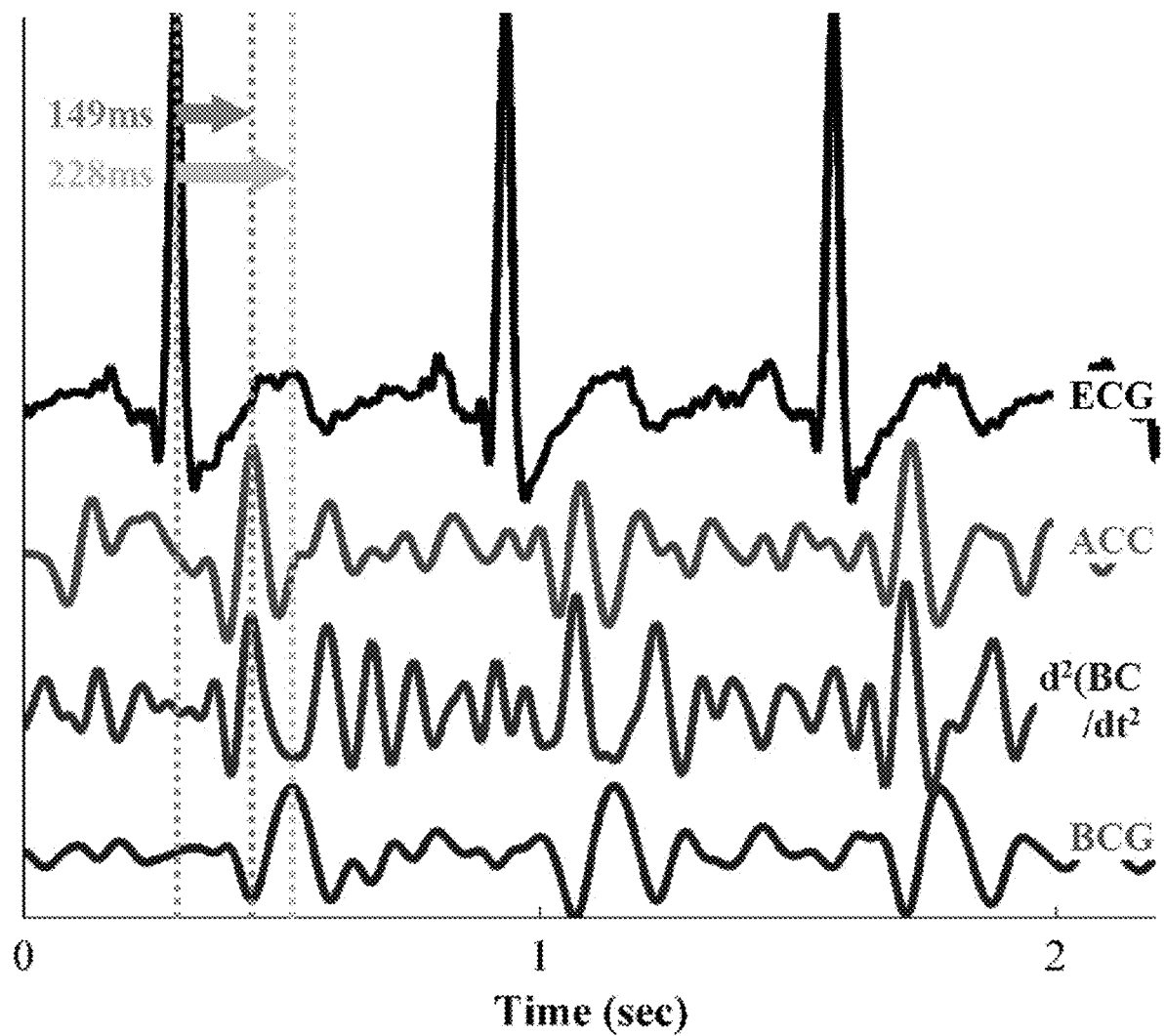
FIG. 2 is a graph of a representative ECG, head-to-foot acceleration (ACC), second-derivative of the ballistocardiogram ($d^2(BCG)/dt^2$), and BCG measurements from one subject. For this recording, the accelerometer was placed on the subject's sternum. The time delays from the ECG R-wave to the main peak of the acceleration and second-derivative BCG signals were identical, at 149 ms, while the time delay from the ECG R-wave to the BCG J-wave peak (R-J interval) was 228 ms, consistent with physiological expectations.

FIG. 1 shows a block diagram of the measurement hardware and setup, and FIG. 2 is a graph of representative signals measured from one subject. As shown, a custom circuit was built and implanted in the modified home weighing scale (BC534, Tanita Corporation, Tokyo, Japan) to interface to the strain gauge bridge in the scale and measure the fluctuations in bodyweight caused by the heartbeat—the head-to-foot BCG signal. An ultra-low noise integrated bridge amplifier and 24-bit sigma-delta analog-to-digital converter (AD7191, Analog Devices, Norwood, Mass.) was used to amplify this differential signal from the strain gauge bridge, and the digitized output was connected to the input port of a microcontroller (1284P, Atmel Corporation, San Jose, Calif.).

The digitized signal, sampled at 120 Hz, was then wirelessly transmitted to the computer using Bluetooth and stored for post-processing and analysis.

The ECG recordings were measured by the BN-EL50 wireless ECG measurement module (BIOPAC Systems, Inc., Goleta, Calif.) with the Ag/AgCl surface electrodes configured for a modified Lead II measurement. The ECG data were transmitted wirelessly from this module to the data acquisition system (MP150WSW, BIOPAC Systems, Inc., Goleta, Calif.) where they were sampled at 1 kHz and stored on the computer.

While the subjects stood on the weighing scale and the BCG and ECG were recorded, the surface acceleration signals in the head-to-foot direction were measured using a small, ultra-low noise accelerometer (356A32, PCB Piezotronics, Depew, N.Y.) attached to various locations on the torso. This accelerometer was selected based on its low spot noise (20 $\mu g_{rms}/\sqrt{Hz}$ at 10 Hz) and total noise (300 $\mu g_{rms}$ for a bandwidth of 1-10,000 Hz), wide signal bandwidth (0.7-5000 kHz, +/−1 dB), and its relatively small size (11.4 $mm^3$) and low weight (5.4 g).

In contrast to micromachined MEMS accelerometers used in previous studies, the self-noise was several times lower: the LIS344ALH (ST Microelectronics, Geneva, Switzerland) accelerometer used in previous studies represents the lowest noise MEMS accelerometer available, with a self-noise of 350 $\mu g_{rms}$ for a bandwidth of 1-50 Hz compared to the 60 $\mu g_{rms}$ for the 356A32 used here. Compared to other instrumentation-grade accelerometers used in previous studies, the weight of the accelerometer was eight times lower, as was the volume: the 4381 (Brüel & Kjer, Naeurum, Denmark) piezoelectric accelerometer used previously weighs 43 g and is a 20.5 mm (diameter)×23.6 mm (height) cylinder compared to the 5.4 g weight and 11.4 $mm^3$ dimensions of the sensor used here.

These choices of accelerometers for previous studies have been driven by the fact that the analysis was focused primarily on dorso-ventral components of cardiogenic surface accelerations of the torso, as compared to head-to-foot components. The dorso-ventral components are larger in amplitude, and, due to the measurement direction being perpendicular to the wall of the chest, mechanical loading of the skin by the sensor would be less of a concern. Since the present invention focuses on head-to-foot accelerations, and the subjects are standing upright, the loading of the skin by a heavy accelerometer would be of great concern, as would an elevated sensor noise floor compromising the accuracy of the measurements. Based on these aspects, the waveforms presented herein are the closest representation of the actual surface accelerations in the head-to-foot direction, are of high signal quality as shown in FIG. 2, and are the most appropriate surface measurements for comparison to BCG recordings from the weighing scale system.

BCG, ECG, and Accelerometer Signal Processing

Figure 3:
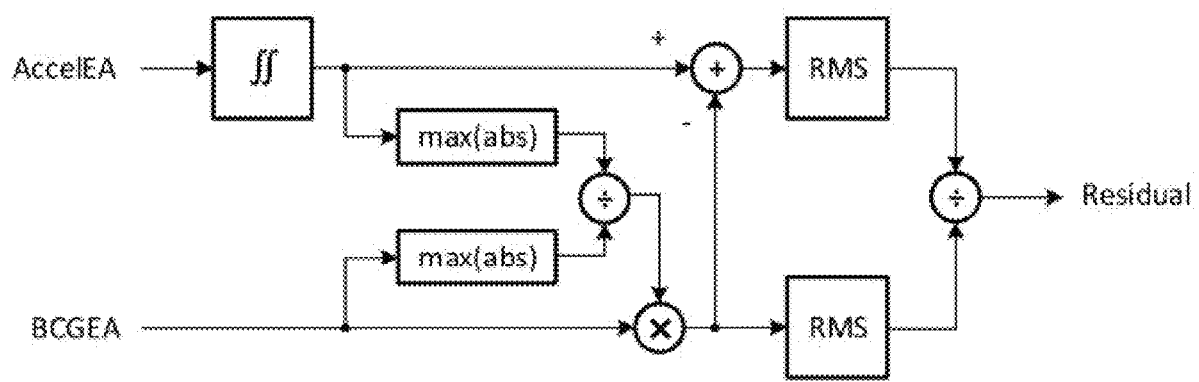
FIG. 3 is a block diagram of signal processing methods for estimating the normalized residual according to an exemplary embodiment of the present invention.
Figure 4:
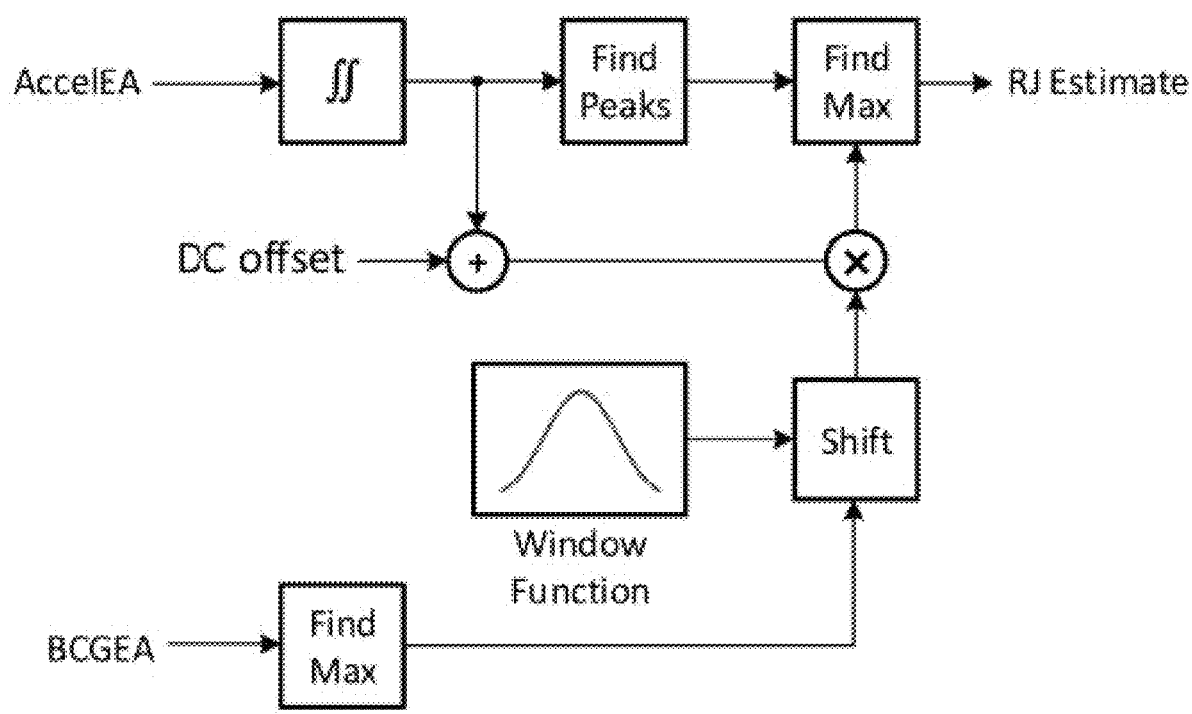
FIG. 4 is a block diagram of signal processing methods for estimating the R-J interval according to an exemplary embodiment of the present invention.
Figure 5:
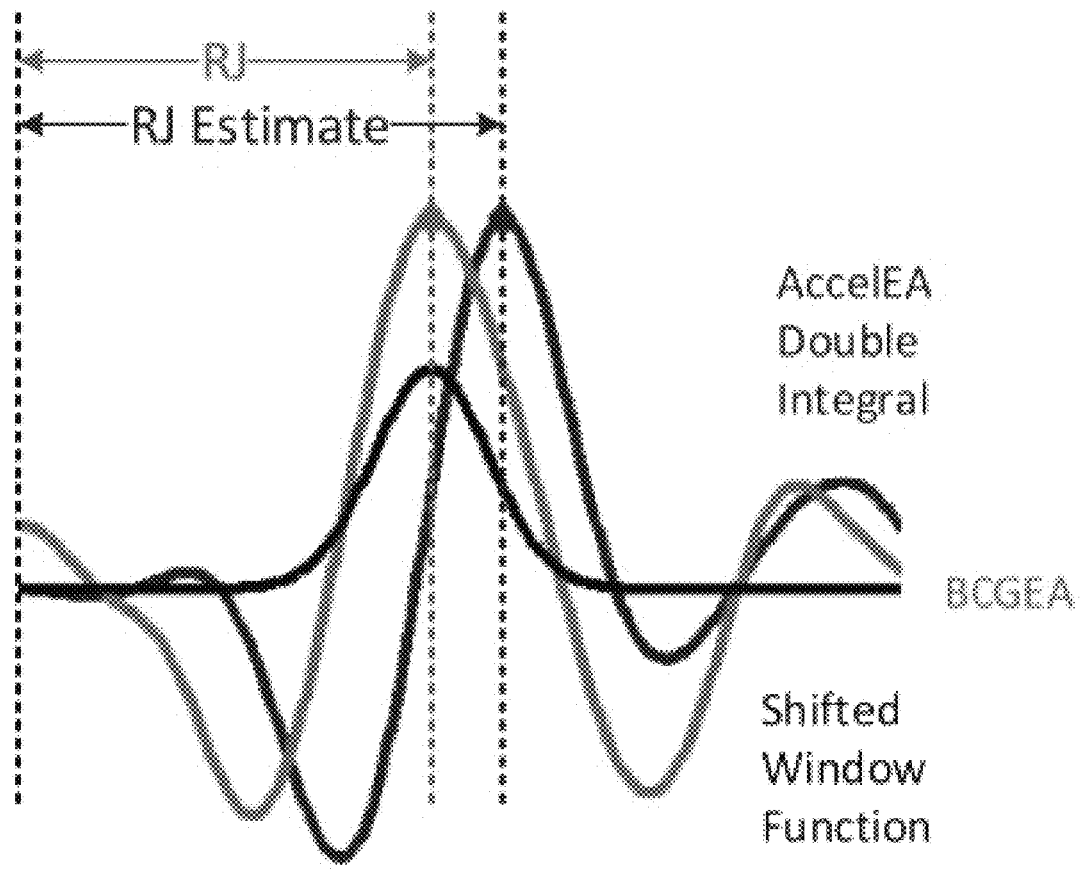
FIG. 5 is a graph of the double-integrated acceleration and BCG signals using the signal processing methods of FIGS. 3-4.

The signal processing comprises pre-processing for reducing electronic noise, baseline wander, and motion artifacts in the signals, and feature extraction from the BCG and acceleration signals. The feature extraction operations are summarized in the block diagrams shown in FIGS. 3-4.

The ECG signal was digitally band-pass filtered (Finite impulse response, FIR, Pass-band: 15-25 Hz, Kaiser window) to extract the QRS complexes, then an automatic peak detection algorithm was employed and checked manually to find the R-wave timings. The BCG was band-pass filtered (FIR, Pass-band: 0.8-15 Hz, Kaiser window) to remove baseline wander and high frequency noise, as was the acceleration signal (Infinite impulse response, IIR, Pass-band: 1-15 Hz, Butterworth). Using the R-wave peaks as a fiduciary point, the BCG and acceleration waveforms were then segmented with a window extending from each R-wave peak timing, $R_i$, to $R_i$+700 ms. The ensemble averages were then computed from these segmented heartbeats. The acceleration ensemble average was then double-integrated using a twice-repeated sequence of trapezoidal integration and low-order polynomial-fitting-based baseline wander estimation and subsequent removal.

For each subject, and each location on the torso, a normalized residual RMSE was then found from the double-integrated acceleration signal compared to the BCG, with a scaling factor first determined based on the ratio of the maximum absolute value amplitude of the signals; a correlation coefficient was also computed.

The R-J interval was calculated for the weighing-scale BCG signal by finding the elapsed time between the previous ECG R-wave peak and the global maximum in the first 400 ms of the BCG ensemble average. The 400 ms window was chosen based on physiological expectations and previous values for normal R-J intervals from the existing literature. The interval between the ECG R-wave and the maximum peak of the vibration signal was measured for the head-to-foot accelerometer signal, and the double-integral of the acceleration, as follows. In initial observations of the double-integrated acceleration, signals, it was noticed that simply using the global maximum over the full window created errors in J-wave peak detection due to the double integration operation amplifying low frequency noise.

One source of low frequency noise is motion or postural sway of the subject. It is known that the standing BCG is more prone to noise from subject motion than stationary techniques such as bed- and chair-based BCG methods where the subject is either supine or seated. Techniques have been developed to reduce this noise in the standing BCG using electromyogram (EMG) signals from the feet as a measure of lower-body muscle contraction and relaxation. Other sources of noise affecting the measurement include low-frequency electrical noise. The low frequency parasitic components from these various sources were shaped by the double integration.

As a result, an algorithm was designed to find the closest large peak to the actual BCG J-wave peak rather than the global maximum. To achieve this, first the indices of all local maxima were located in the first 400 ms of the acceleration ensemble average. Then the acceleration ensemble average was offset with a positive DC bias and multiplied by a Gaussian window function centered on the true J-wave peak. This signal was evaluated at the samples corresponding to the local maxima and the absolute maximum among them was selected as the best estimate for the J-wave peak.

In this way, the estimated J-wave peak was located with preference first to peaks that were closest to the true J-wave peak and then for peaks that were large. (A large peak in the acceleration signal that was slightly farther from the true J-wave peak will be selected over a much smaller peak closer to the true J-wave with the width of the Gaussian window function determining the balance between peak size and distance from true J-wave.) Additionally, an analysis of these error metrics against heart rate was performed, and no significant correlations were found.

Experiments and Statistical Analysis

For one subject with representative acceleration and BCG waveform amplitude and morphology tri-axial acceleration signals were measured from several locations on the torso and head and plotted them for visual analysis and comparison.

For all subjects, the head-to-foot accelerations were measured at three locations—sternum, PMI, and lower back (center-of-mass, COM)—simultaneously with the ECG and BCG. The best location for each subject was determined based on the lowest normalized residual and the highest correlation coefficient. The statistical significance (at the p<0.05 level) of the differences in both normalized residuals and correlation coefficients for the different locations for all subjects were assessed using Student's t-test.

For the R-J intervals, Bland-Altman methods were used to assess the agreement between the two accelerometer-derived R-J intervals (one from the acceleration signal itself, and one from the double-integrated acceleration signal) and the BCG-derived "gold" standard R-J interval. The bias and confidence interval for both of these techniques were compared, and determined whether or not a body-worn accelerometer combined with ECG could yield an accurate estimate of the R-J interval.

Results and Discussion

Figure 6:
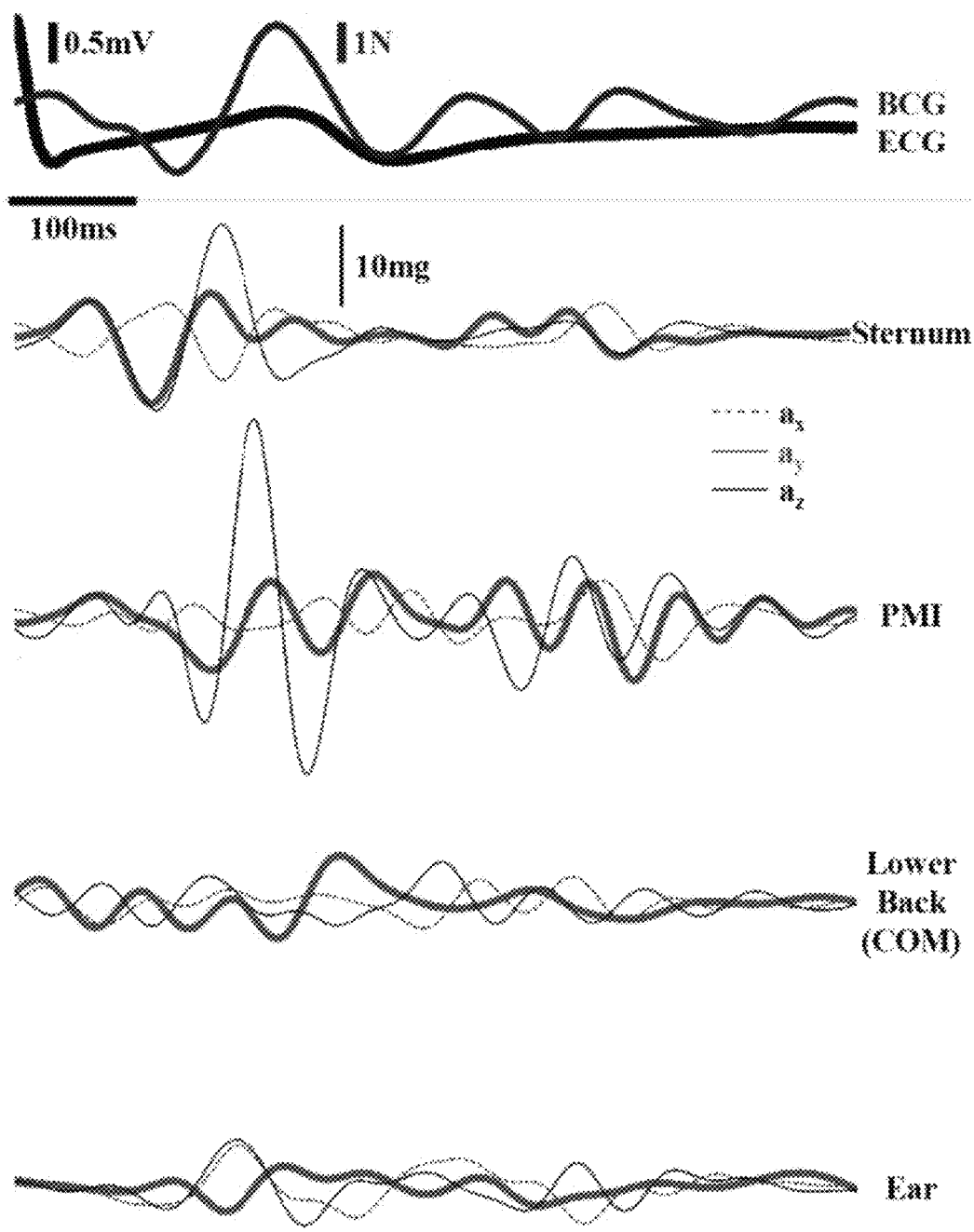
FIG. 6 are ensemble averaged ECG and BCG (top), and tri-axial acceleration waveforms for one subject with the accelerometer placed at the following positions: the sternum, point of maximal impulse (PMI), lower back (COM), and ear. All signals are shown on the same x-axis (time), the ECG and BCG scale bars are shown for their respective amplitudes, and the 10 mg amplitude scale bar applies to all acceleration signals.

Influence of Sensor Placement on Signal Morphology and Timing: Results from One Subject The ensemble averaged acceleration waveforms in all three axes—with x as lateral, y as dorso-ventral, and z as head-to-foot directions—are shown in FIG. 6 alongside the simultaneously-acquired ECG and BCG signals for one subject. Note that the head-to-foot acceleration is greatest at the PMI, and decreases at the sternum and lower back. For the dorso-ventral direction, the time delay between the ECG R-wave and the largest negative peak in the acceleration waveform is shortest at the sternum, then the PMI, then longest at the lower back. The recording from the ear appears to be the smallest in terms of peak-to-peak accelerations, and is delayed in time compared to the sternal signal.

Statistical Results from All Subjects

TABLE I shown in FIG. 7 shows the normalized residual and correlation coefficient values for all subjects for the three positions. The position with the lowest residual is denoted by an asterisk (*), and the position with the highest correlation coefficient by a dagger (†). The PMI was the best location in terms of lowest residual and highest correlation coefficient for only three of the fifteen subjects; the lower back was the best location in terms of lowest residual for three of fifteen subjects, but highest correlation coefficient for six subjects. The sternum was the best location of the three, with significantly lower normalized residual compared to the PMI and lower back for the overall subject population (p<0.05). Considering only the results from the best of three locations for all subjects, the average (±σ) normalized residual and correlation coefficient are 0.83 (±0.22) and 0.83 (±0.07).

Finally, following the trend shown in FIG. 6 for one subject, the peak-to-peak acceleration amplitude was significantly (p<<0.01) highest on average for all subjects with the sensor placed at the PMI (61.3±26.8 mg), then the sternum (32.6±12.6 mg), then the back (16.3±10.5 mg), and the minimum location occurred significantly later (p<0.05) in the cardiac cycle at the lower back (224.0±35.8 ms) compared to the sternum (176.2±81.1 ms).

R-J Interval Comparisons

Figure 8:
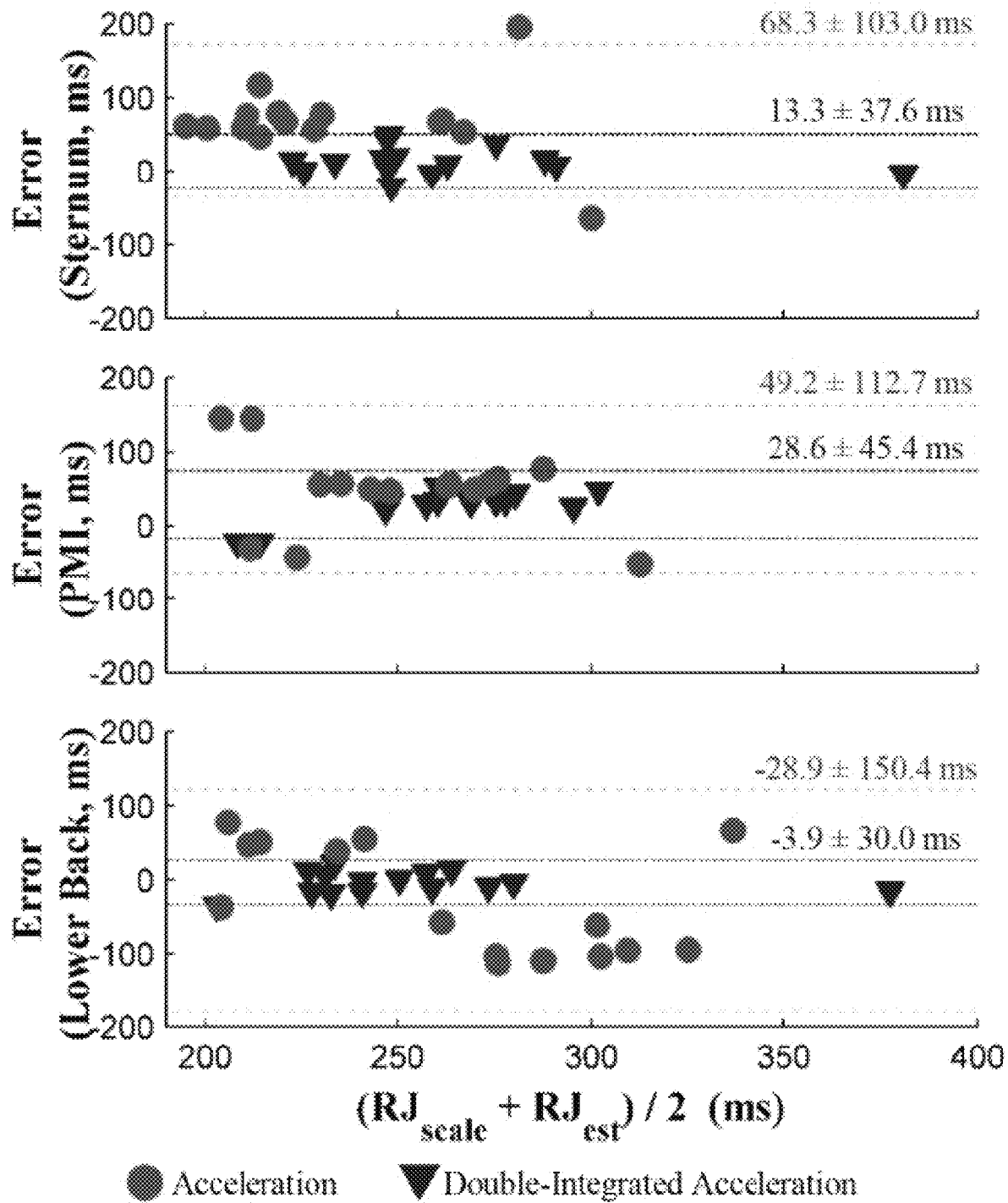
FIG. 8 presents three graphs, being Bland Altman plots showing agreement between ECG R-wave to BCG J-wave intervals derived from the weighing scale BCG signal ("gold" standard) compared to corresponding R-J intervals derived from the acceleration and double-integrated acceleration waveforms measured at the sternum, PMI, and lower back. For each location, the confidence intervals (95%) are also plotted for each estimate, and the bias±confidence interval is shown. The best agreement was found in the lower back measurement, after taking the double integral of the head-to-foot acceleration waveform. Using the acceleration waveform itself always resulted in poorer bias and confidence interval for R-J interval estimation.

FIG. 8 shows three Bland-Altman plots of agreement between the "gold" standard R-J interval measurement (the interval between the ECG R-wave and the weighing scale BCG J-wave) and the acceleration or double-integrated acceleration waveforms from all three locations on the body. With the accelerometer located at the sternum or lower back, the R-J interval derived using the double-integrated acceleration signal showed good agreement with the weighing scale. The best location for R-J interval estimation was found to be the lower back, with a bias of −3.9 ms and a confidence interval of ±30 ms. Using the acceleration waveform itself provided poor agreement with weighing scale R-J intervals, with both a large bias and wide confidence interval.

DISCUSSION

The results confirm that although a body-mounted accelerometer can be used for BCG measurement, the acceleration waveform itself should not be interpreted using standard BCG nomenclature or feature extraction techniques. Rather, an ensemble averaging and double integration operation can be used to transform the acceleration waveform into a COM BCG signal, from which standard BCG feature extraction techniques can be applied. Additionally, although accelerations measured at the PMI have the largest amplitude—and thus the highest electronic SNR—the PMI is the worst location for both matching the BCG signal morphology and for extracting the R-J interval feature. This reinforces the importance of optimizing physiological sensing systems and approaches based on the physiology and findings from human subjects studies, rather than using engineering principles alone.

The best location for placing the accelerometer for wearable BCG measurements is subject-dependent, indicating that for optimal results an initial calibration step likely is needed. For example, a subject could stand on the BCG-equipped weighing scale while wearing an accelerometer on the torso, and the transfer function between the measurements could be modeled mathematically. For most measurements, the sternum is the best location for mounting the sensor, as it produced the lowest average residual (best morphological match) compared to the COM BCG and accurate R-J interval feature extraction. For applications requiring best timing precision in assessing the R-J interval, the lower back placement should be used: this positions the accelerometer as closely as possible to the COM of the person, thus closely mirroring the COM movements which are measured with the scale.

Finally, these results suggest that in addition to the hemodynamic components at the origin of these low frequency (<20 Hz) vibration signals of the torso, there are other components that are localized at the heart: for example, the movement of the heart itself.

The present invention presents innovative methodologies that can be used to extract clinically relevant BCG features based on acceleration measurements from different locations on the torso, and provides promising evidence for these methods based on preliminary findings from human subjects studies. The methodologies potentially can reduce some of the confusion in the scientific community regarding the relationship between traditional "fixed" BCG measurements and wearable BCG measurements, and reiterates the importance of sensor placement for interpreting results.

While the results appear promising, a few limitations should be mentioned. Although double integration improved the accuracy of the R-J interval measurement, and therefore the measurement of changes in contractility, this method has not been validated for patients with heart failure or other cardiac abnormalities. Additionally, the standing BCG method used herein can exhibit more noise from motion and postural sway than BCG methods for which the patient is seated or supine.

II. Identification Techniques for Improved Wearable Hemodynamics Assessment

As discussed above, simply interpreting the wearable BCG signal as a displacement BCG yields incorrect cardiac assessments, specifically of the R-J interval. Thus, in another exemplary embodiment of the present invention, a framework for reconstructing the WS BCG from the wearable sensor via a calibration, or training, step is built. Furthermore, it is demonstrated for the first time that WS BCG can even be measured from the vertical accelerations of the wrist.

Figure 9:
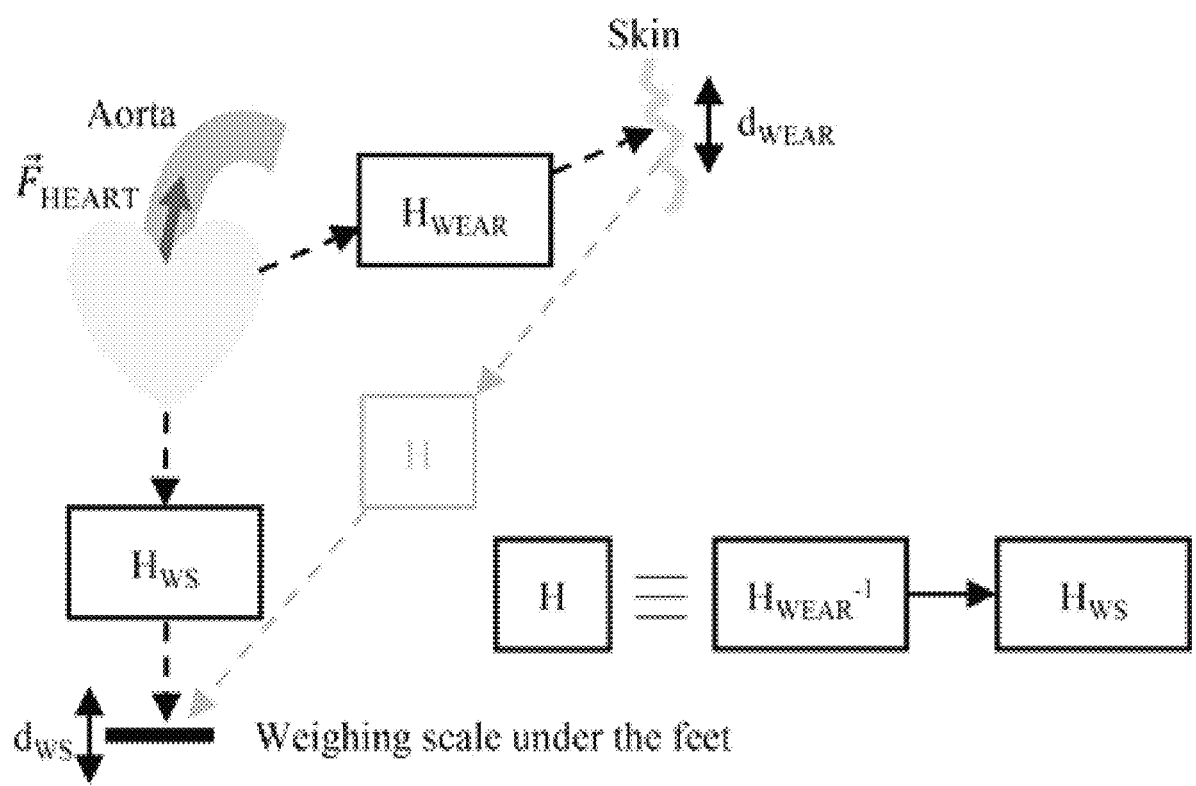
FIG. 9 is a block diagram modeling the relationship between a wearable BCG and the weighing scale ballistocardiogram (WS BCG). Ejection of blood into the aorta causes local and whole-body displacement perturbations at the surface of the skin and the feet via two different mathematical systems.

Although the wearable signal differs from these two widely studied signals, it is related to them via the mechanics of the body. These underlying relationships can be leveraged to cross domains between different sensor modalities. As will be shown, the relationship between the wearable BCG and the WS BCG shown in FIG. 9 is detailed, an improved numerical integrator is developed to estimate the displacement of a wearable sensor from its acceleration, a framework to resolve the WS BCG from the wearable BCG is built, and preliminary validation of this framework with data from human subjects is provided.

Physical Overview and Hypotheses

Previous Studies

Comparison and refinement of different types of BCG measurements has been approached in various ways. Electric filters were developed to correct the frequency responses of displacement and velocity BCG beds. More recently, others noted several differences between 3-D acceleration BCG measurements from two locations on the spine in the time and frequency domain. The issue of comparing BCG displacements, velocities, and accelerations has also been raised, wherein it was remarked that there is similarity of the HF BCG (displacement) to the second derivative (acceleration) of the ULF BCG.

In this exemplary embodiment of the present invention, a framework is developed for converting between different BCG modalities in order to ease such dependence on the specific hardware used.

Hypotheses

The WS BCG is a measurement of displacements resulting from cardiac ejection of blood into the vasculature. The WS BCG signal is examined in the vertical, or head-to-foot, axis when the subject is standing upright. Recently, several researchers have attempted to measure BCG signals from wearable devices, most notably a miniature accelerometer attached to the surface of the skin. Although this approach may yield continuous BCG recording in naturalistic environments, there are several outstanding scientific questions that must be addressed to properly compare between the two domains—wearable versus other BCG modalities.

Whole-body displacements most closely match those at the surface of the skin when the wearable sensor is located at regions on the body that are well coupled to the rigid skeletal system. Specifically, as disclosed above, acceleration measurements at these locations closely matched the second derivative of the WS BCG. In this exemplary embodiment, the relationship between these two fundamentally different BCG measurements are examined, and an innovative method to reconstruct the WS BCG from the wearable signal is developed. To achieve this reconstruction, the present method relies heavily on the following hypothesis: a first-order approximation of the WS BCG can be obtained by twice integrating the wearable BCG.

To motivate the need for double integration, it is important to first highlight one aspect of the wearable BCG vis-à-vis the WS BCG. The wearable BCG disclosed herein is a measure of the acceleration of the sensor's mass on the surface of the skin. By contrast, the weighing scale is a mass-spring-dashpot system of the form shown in Equation 1 where the damping b and mass m terms are nearly zero.

$$F = kx + by + ma \quad (1)$$

$$F = kx \quad (2)$$

This is evident by the scale's frequency response. As a result, the displacement term containing the spring constant k is dominant: Hooke's Law (Equation 2) governs the motion of the WS platform, and the WS BCG signal is directly proportional to the platform's displacement. The wearable BCG and WS BCG are related primarily by the integral operator. When modeling the relationship between the wearable and WS BCG signals, it is important to first integrate the wearable acceleration signal twice in order to obtain an estimate of the sensor's displacement.

The a priori knowledge about the physical behavior of the wearable sensor was leveraged to improve this displacement estimate. Since the accelerometer was physically attached to the skin and not able to move freely in space, it was assumed that nearly zero low-frequency energy should exist in the acceleration, velocity, and displacement. (If low-frequency components in these signals were allowed to persist, small errors in the acceleration measurement would accumulate into large velocities and displacements via the integral operators, and would thus, incorrectly signify a slow drift of the sensor's position away from the thorax.)

Figure 10:
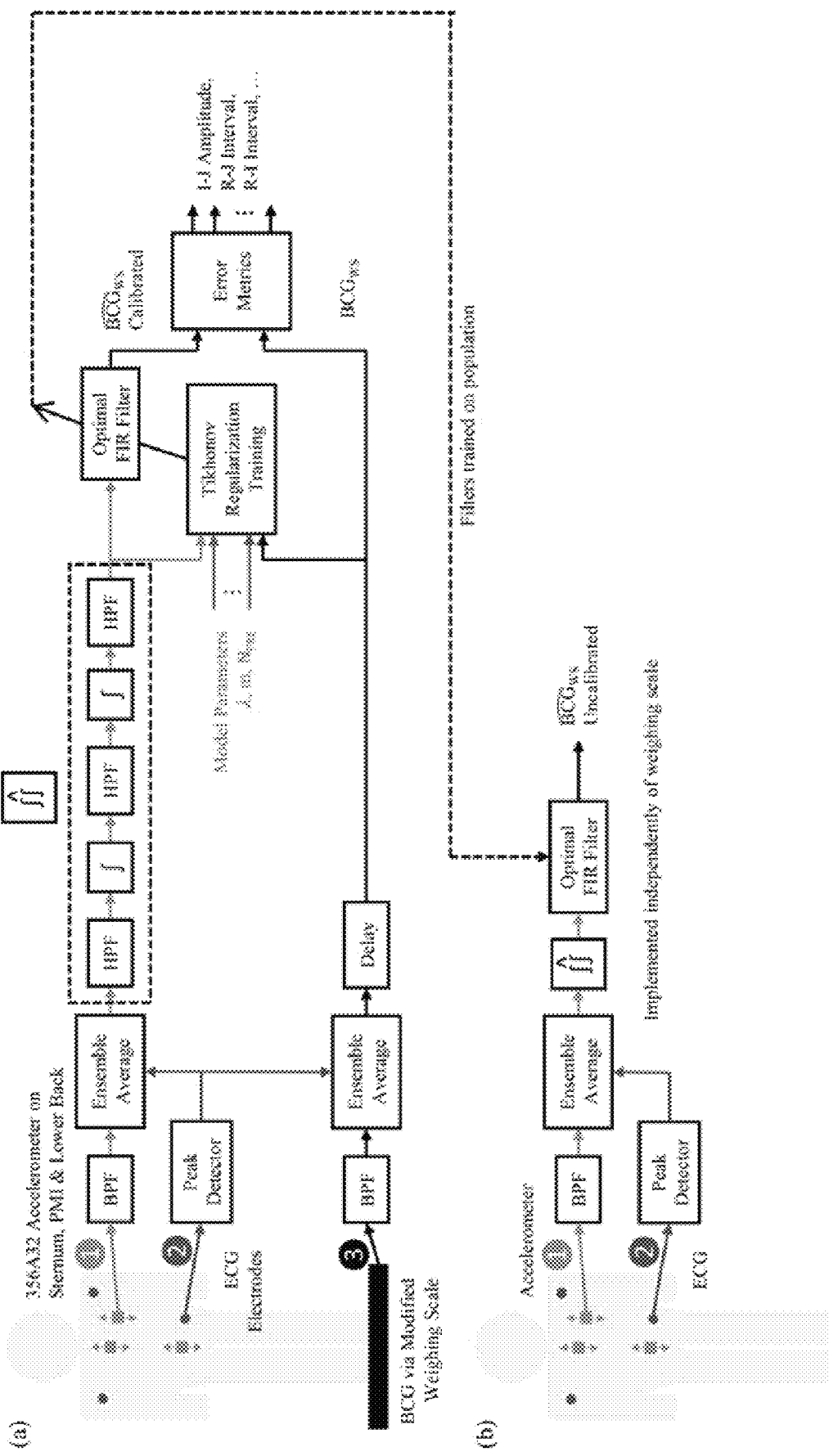
FIGS. 10(a) and (b) are block diagrams showing exemplary signal processing systems according to the present invention. The calibrated configuration is shown in 10(a), where the system is first trained on the individual, and 10(b) shows the uncalibrated configuration, where the system is pre-trained on a population of subjects.

Therefore, numerical integration was performed in series with high-pass filters as shown in FIGS. 10(*a*) and (*b*) to eliminate spurious low-frequency energy, and the cutoff frequency of the filters was determined empirically. The output of this sequence of operations was an estimate of the wearable sensor's displacement as a function of time, which was then used in subsequent steps to estimate the displacement of the weighing scale.

To estimate the WS displacement, the relationship between the wearable and WS BCG are modeled as a mathematical system H as shown in FIG. 9. In this model, the input to H is the wearable sensor's estimated displacement and the output is the WS BCG. Single-input-single-output (SISO) mechanical systems, such as the classic spring-mass-dashpot system, are generally causal as perturbations at the input result in changes at the output only after they occur. However, since the genesis of energy in mechanical cardiac signals like the BCG is myocardial contraction and relaxation inside the thorax, and the resultant ejection of blood into the aorta, it is hypothesized that wearable BCG signals recorded with an accelerometer on the surface of the body and WS BCG signals will both be coupled to the same source, the heart muscles and central blood movement, via two different unknown mechanical systems in the body.

In this situation, the outputs of two SISO systems, $H_{WEAR}$ and $H_{WS}$, are the displacements of the wearable and WS BCG signals, and these two systems share a common input originating from the heart. If this hypothesis is accurate, H will be non-causal because it involves the inverse of a causal system, $H_{WEAR}$, in series (cascaded) with $H_{WS}$. Because inverting a causal system in general results in a non-causal one, the overall series system will also in general be non-causal.

Consequently, it is posited that an approximation of H can be obtained via system identification by training a non-causal linear finite impulse response (FIR) filter $\hat{H}$ with simultaneous recordings of the wearable and WS BCG. Although H is almost certainly an infinite impulse response (IIR) system due to its mechanical origins in $H_{WEAR}$ and $H_{WS}$, an FIR filter of sufficient length can approximate an IIR system provided that the latter is stable. As instability would imply oscillations in the mechanical systems over time of sustained or increasing magnitude, stability of H is almost certainly a reasonable assumption. Therefore, if $\hat{H}$ can be made long enough to include most of the energy in the true system, $\hat{H}$ should provide a good reconstruction of the WS BCG from the wearable BCG. The methods used to find $\hat{H}$ and the error metrics used to quantify its goodness of fit are explained.

Methods

Hardware and Data Acquisition

The measurement hardware and setup is not unlike that shown in FIG. 1. Wearable BCG measurements were made with a high-resolution instrumentation-grade accelerometer oriented such that the foot-to-head direction was positive. In the same way as disclosed above, a small, ultra-low noise accelerometer (356A32, PCB Piezotronics, Depew, N.Y.) attached to various locations on the torso. This accelerometer was selected based on its low spot noise (20 $\mu g_{rms}/\sqrt{Hz}$ at 10 Hz) and total noise (300 $\mu g_{rms}$ for a bandwidth of 1-10,000 Hz), wide signal bandwidth (0.7-5000 kHz, +/−1 dB), and its relatively small size (11.4 mm$^3$) and low weight (5.4 g).

WS BCG recordings in the same axis were measured with a modified weighing scale that also captured an ECG with handlebar electrodes. A custom circuit was built and implanted in the modified home weighing scale (BC534, Tanita Corporation, Tokyo, Japan) to interface to the strain gauge bridge in the scale and measure the fluctuations in bodyweight caused by the heartbeat—the head-to-foot BCG signal. An ultra-low noise integrated bridge amplifier and 24-bit sigma-delta analog-to-digital converter (AD7191, Analog Devices, Norwood, Mass.) was used to amplify this differential signal from the strain gauge bridge, and the digitized output was connected to the input port of a microcontroller (1284P, Atmel Corporation, San Jose, Calif.).

The digitized signal, sampled at 120 Hz, was then wirelessly transmitted to the computer using Bluetooth and stored for post-processing and analysis.

The ECG was sampled at 1 KHz and also transmitted via Bluetooth.

A second ECG waveform was captured simultaneously with Ag/AgCl gel electrodes to synchronize the wearable BCG and WS BCG recordings, which were captured with separate data acquisition units and sample rates. The second ECG recordings were measured by the BN-EL50 wireless ECG measurement module (BIOPAC Systems, Inc., Goleta, Calif.) with the Ag/AgCl surface electrodes configured for a modified Lead II measurement. The ECG data were transmitted wirelessly from this module to the data acquisition system (MP150WSW, BIOPAC Systems, Inc.), where they were sampled at 1 kHz and stored on the computer. The data acquisition system recorded the wearable BCG simultaneously at the same sample rate of 1 kHz.

All signals were recorded by a PC, resampled to a sample rate of 1 kHz, synchronized via cross correlation of the two ECG recordings, and analyzed offline. The coupling of the accelerometer to the skin can influence the system frequency response for the accelerometer BCG measure. The exact manner in which this impacts system frequency response is unknown and can depend on many variables such as body fat, skin softness, and bone coupling. Thus, a purpose of this investigation was is to find a method for identification of the system without such characterization.

Human Subjects

Fifteen healthy subjects with differing anthropometrics were recruited for this study approved by the GT IRB. Among these subjects were ten men and five women aged 22 to 57. Body mass ranged from 49 to 104 kg and height spanned 160 to 196 cm. The subjects were asked to wear three gel electrodes for measuring the ECG while also standing on a modified weighing scale to simultaneously capture the WS BCG. Additionally, subjects were asked to wear an accelerometer adhesively attached to the skin at each of three locations on the body: the body of the sternum halfway between the manubrium and the xiphoid process, the PMI on the pectorals directly above the heart, and the lumbar vertebrae at the lower back near the body's center-of-mass. The sternal BCG recorded in this study is also known as the "vertical sternal seismocardiogram."

The subjects were asked to stand as still as possible on the scale while wearing the ECG electrodes and the accelerometer, and recordings approximately 1 min in length were captured with the accelerometer at each of the three locations resulting in 45 total recordings.

In addition to the fifteen-subject trials, recordings were also made on one individual over a span of nine consecutive days to determine if cardiovascular health could be monitored over time via the wearable BCG. The wearable sensor was placed at the sternum, PMI, and lower back as before; however, additional recordings were also taken at the wrist.

For the wrist trials, the wearable sensor was attached to the body where a person would typically place the face of a wrist watch. Cross validation was not used. Instead, $\hat{H}$ was trained on data from the first day, the WS BCG was reconstructed from the wearable BCG on each day using $\hat{H}$, and these reconstructions were evaluated using the same error metrics as before.

Cross Validation and Error Metrics

K-fold cross validation is a technique commonly used to perform model selection in statistical and machine learning problems. K-fold cross validation is the process of randomly partitioning a dataset into k equal-size subsamples and performing the following procedure k times (folds): one subsample is used to validate the results of the algorithm after training the algorithm with the other subsamples. The k results are then averaged and a single estimation is produced.

To use this tool on the present dataset, the BCG and ECG waveforms were split in each of the 45 recordings into individual heartbeats. Within each recording, five equal-sized sets of heartbeats were randomly partitioned. The signal processing steps described in the next section were performed on each recording five times, each time using four heartbeat sets to train the model (the training set) and using the remaining heartbeat set to perform a reconstruction of the WS BCG from the wearable BCG (the validation set). K=5 was chosen as a tradeoff between immunity to overfitting for large values of K and low SNR of the ensemble average when using a small number of heartbeats in the validation set.

Three error metrics were calculated from each fold's reconstructed WS BCG. These error metrics were the R-J interval, R-I interval, and I-J amplitude. These values are classical BCG measures of different cardiac metrics, and a good reconstruction of the WS BCG should accurately reproduce these values. The average of these three values across all recordings and folds was determined and used as a composite error score to select each parameter in the model. 1-D error traces were generated by calculating the composite error score via cross validation for different values of one parameter while holding other parameters constant. Likewise, 2-D error traces were performed by varying two parameters.

Signal Processing

FIGS. 10(a) and (b) show block diagrams of the signal processing subsystems. First, band-pass filtering was performed on the BCG signals to eliminate out-of-band noise. The passband for these filters was 0.8-8.0 Hz. Although the BCG contains frequency components higher than 8.0 Hz, it was found that removing them improved the reconstruction.

Next, a preprocessing step was used to increase the SNR of the two BCG signals. The SNR of repeating events can be improved by leveraging the uncorrelated nature of the noise via ensemble averaging. An ensemble average of each signal was, therefore, produced by calculating the sample-by-sample mean with respect to fiducial points synchronous to the cardiac cycle. Similar to previous studies, the R-peak in the ECG was used as the fiducial point. The minimum R-R interval for each recording, $RR_{MIN}$, was used as the total number of samples in the ensemble average including and following the R-peak.

A smaller $N_{PRE}$ were also included in the ensemble average to increase the total number of samples; the total number of samples in the ensemble average was, therefore, $RR_{MIN}+N_{PRE}$. Since cross validation was used, separate ensemble averages were constructed for the training and validation sets.

Finally, an estimate for the accelerometer displacement was determined via double integration and high-pass filtering. Numerical integration was performed with trapezoidal integrators, and high-pass filters were implemented with moving average subtractors. The output of each high-pass filter was its input subtracted by its moving average, and the length of the moving average was the same for all the filters. The optimal length was determined empirically with a 1-D error trace and found to be 100 samples for a sample rate of 1000 Hz. This resolves to a cutoff frequency of 6.0 Hz (corresponding to the filter's—3 dB point) and a maximum passband ripple of 1.45 dB.

System Identification Via Least-Squares Regression

A training step was used to find the impulse response of $\hat{H}$. For any FIR filter, there are three parameters that must be optimized with the objective of achieving generalization, and thereby, avoiding overfitting: (1) causality of the system, (2) length of the filter, and (3) values for the filter weights. The following approach was used for optimizing these three parameters.

First, the WS BCG ensemble average was modified with a variable delay. A zero delay resulted in the best-fit causal impulse response, while delays greater than zero produced a non-causal FIR. Performing cross validation for each case revealed that causality had a large impact on the reconstruction accuracy.

Second, the length of the filter was determined using 2-D error tracing. A sweep of filter lengths from 1 to 800 samples and $N_{PRE}$ from 0 to 400 was performed and the values of these two parameters corresponding to the minimum composite error score from cross validation were found.

Third, the impulse response of the optimal FIR filter was found via least-squares regression. In a typical discrete linear system, an unknown signal x modified by a known linear transform A produces a known output b as shown in Equation 3:

$$Ax=b \quad (3)$$

To find the best-fit FIR filter of order m to transform one signal f of length N into another signal d, a linear equation can be constructed in the same form. In this case, the A matrix contains samples from the input signal f, b contains samples from the desired output signal d, and x is a 1-D vector of FIR coefficients, or taps. This process is broadly named least-squares filtering.

The explicit form of A, b, and x is shown in Equations 4-6. As used herein, signal f is the vector of samples from the wearable BCG displacement ensemble average, d is the vector of samples from the (possibly delayed) WS BCG ensemble average, and x contains the adaptive filter coefficients.

$$A = \begin{bmatrix} f[m] & f[m-1] & \cdots & f[1] \\ f[m+1] & f[m] & \cdots & f[2] \\ \vdots & \vdots & \ddots & \vdots \\ f[N] & f[N-1] & \cdots & f[N-m+1] \end{bmatrix} \quad (4)$$

$$b = \begin{bmatrix} d[m] \\ d[m+1] \\ \vdots \\ d[N] \end{bmatrix} \quad (5)$$

$$x = \begin{bmatrix} h[1] \\ h[2] \\ \vdots \\ h[m] \end{bmatrix} \quad (6)$$

This particular form of A, b, and x is sometimes called the covariance method because it uses only data that is explicitly available and does not assume that samples outside of the available data window are zero. In this context all of the samples in the ensemble average are used and it was not assume that samples outside of the ensemble average window are zero. This results in a matrix equation that is more computationally expensive to solve but improves the accuracy of the solution.

Tikhonov Regularization

The regression was also regularized to reduce overfitting. Since the data included imperfections from various sources such as electrical noise, postural sway of the subjects, and motion artifacts from small movements like head-tilts, a least squares solution would overfit the training data reducing the accuracy of the reconstruction. Tikhonov regularization was employed to mitigate this effect.

The ordinary least-squares solution x is that which minimizes the square of the L2-norm of the error as shown in Equation 7. The solution $\hat{x}$ is shown in Equation 8.

$$\arg_x \min(\|Ax-b\|^2) \quad (7)$$

$$\hat{x} = (A^T A)^{-1} A^T b \quad (8)$$

Since ordinary least-squares is highly sensitive to noise, $\hat{x}$ can be regularized by adding a term to the minimization expression as shown in Equation 9.

$$\arg_x \min(\|Ax-b\|^2 + \|\Gamma x\|^2) \quad (9)$$

In this updated loss function, $\Gamma$ is a Tikhonov matrix whose effect is to give preference to certain solutions. For this study, the scaled identity matrix in Equation 10 was chosen.

$$\Gamma = \lambda I \quad (10)$$

This particular Tikhonov matrix causes the solution vector $\hat{x}$ to shrink toward the origin. Small values of $\lambda$ result in overfitting while large values of $\lambda$ result in underfitting. In other words, the solution approaches the ordinary least squares solution as $\lambda \to 0$ and zero as $\lambda \to \infty$. The optimal value of $\lambda$ was $6.7 \times 10^{-4}$ when displacements were expressed in meters as determined with a 1-D error trace. (Tikhonov regularization is also known as ridge regression in statistics, and this kind of error trace is often called a ridge trace in that field.) The Tikhonov-regularized solution is shown in Equation 11.

$$\hat{x} = (A^T A + \lambda^2 I)^{-1} A^T b \quad (11)$$

In this case, the solution $\hat{x}$ is the FIR filter's vector of coefficients and the impulse response of $\hat{H}$.

Evaluating Results

The methods described above were evaluated using the composite error score. 2-D error traces were generated by sweeping the $N_{PRE}$ and filter lengths with cross validation on the entire dataset. The optimal values for these two parameters were chosen by finding the minimum average composite score for each of the three locations on the body to determine if these parameters depended on the wearable sensor's location. This process was performed separately for the causal and non-causal cases to support or refute the proposed causality hypothesis. Additionally, the individual error values were extracted from the cross validation step for the sternum, PMI, and lower back. Finally, uncalibrated reconstructions were also made by using the average FIR filter for each body location across all subjects to reconstruct the WS BCG for each subject. The error scores for these uncalibrated reconstructions were used to evaluate whether it would be possible to achieve accurate results without the training step.

Results and Discussion

Results for all Subjects

Figure 11:
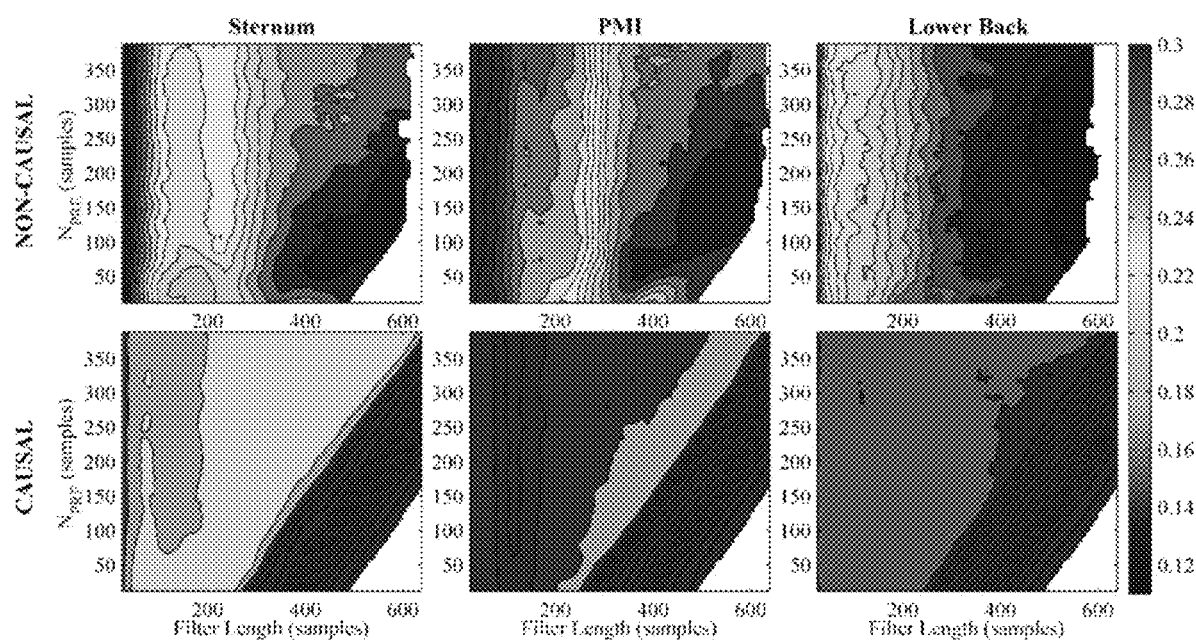
FIG. 11 presents a series of contour plots of 2-D error traces for the causal and non-causal BCG reconstructions from the wearable BCG at the sternum, PMI, and lower back. The plots were generated on the same grey scale so that comparisons can be made more easily between them. The causal filters resulted in very large errors while the non-causal filters performed well with an average error across the three error metrics of about 12% at the optimal filter length and number samples before the R-peak ($N_{PRE}$).

FIG. 11 shows 2-D error traces for causal and non-causal reconstructions of the WS BCG for each wearable sensor location on the body. Non-causal filters clearly resulted in a much better reconstruction than the causal ones, suggesting that the underlying impulse response of H is indeed non-causal. There was little difference in the optimal $N_{PRE}$ and filter length between the different locations on the body, although the optimal $N_{PRE}$ for the lower back was slightly longer than the other two.

The optimal $N_{PRE}$ and filter length (m) in samples were 141 and 558 for an overall error of 0.1194 at the sternum, 145 and 550 for an error of 0.1240 at the PMI, and 162 and 550 for an error of 0.1124 at the lower back. The lower back was still the best location to wear the sensor, but only slightly. The raw error metrics from cross-validation testing for each subject with these values for $N_{PRE}$ and m are shown in FIG. 12, TABLE II.

While FIG. 11 shows that the best reconstructions were from the lower back for short filter lengths, suggesting that the lower back displacement is probably closest to the WS BCG and agreeing with the results of the above embodiment, it is interesting to note that when the techniques used were applied the difference between wearable locations almost completely disappeared. After an initial training step, or calibration, reconstructing the WS BCG from the wearable BCG was just as accurate from one location on the body as another. As a result, the wearable device could be placed on any location on the body by the user themselves, and after a calibration step with the weighing scale, the WS BCG could be accurately reconstructed for the remainder of use.

Figure 13:
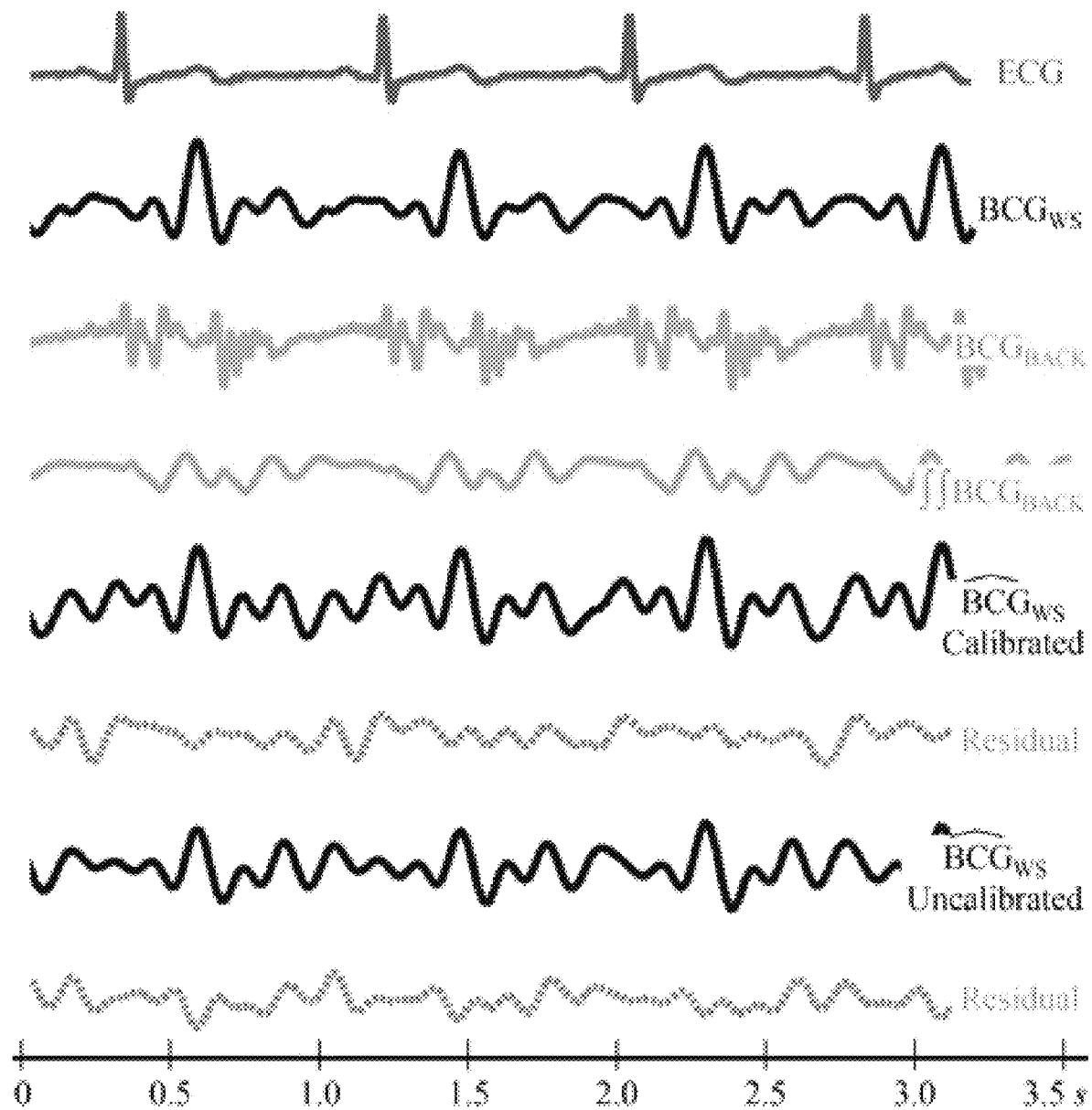
FIG. 13 presents a series of waveforms showing the reconstruction process of a recording with a wearable sensor placed at the lower back. The calibrated WS BCG reconstruction is visibly superior to the uncalibrated one.
Figure 14:
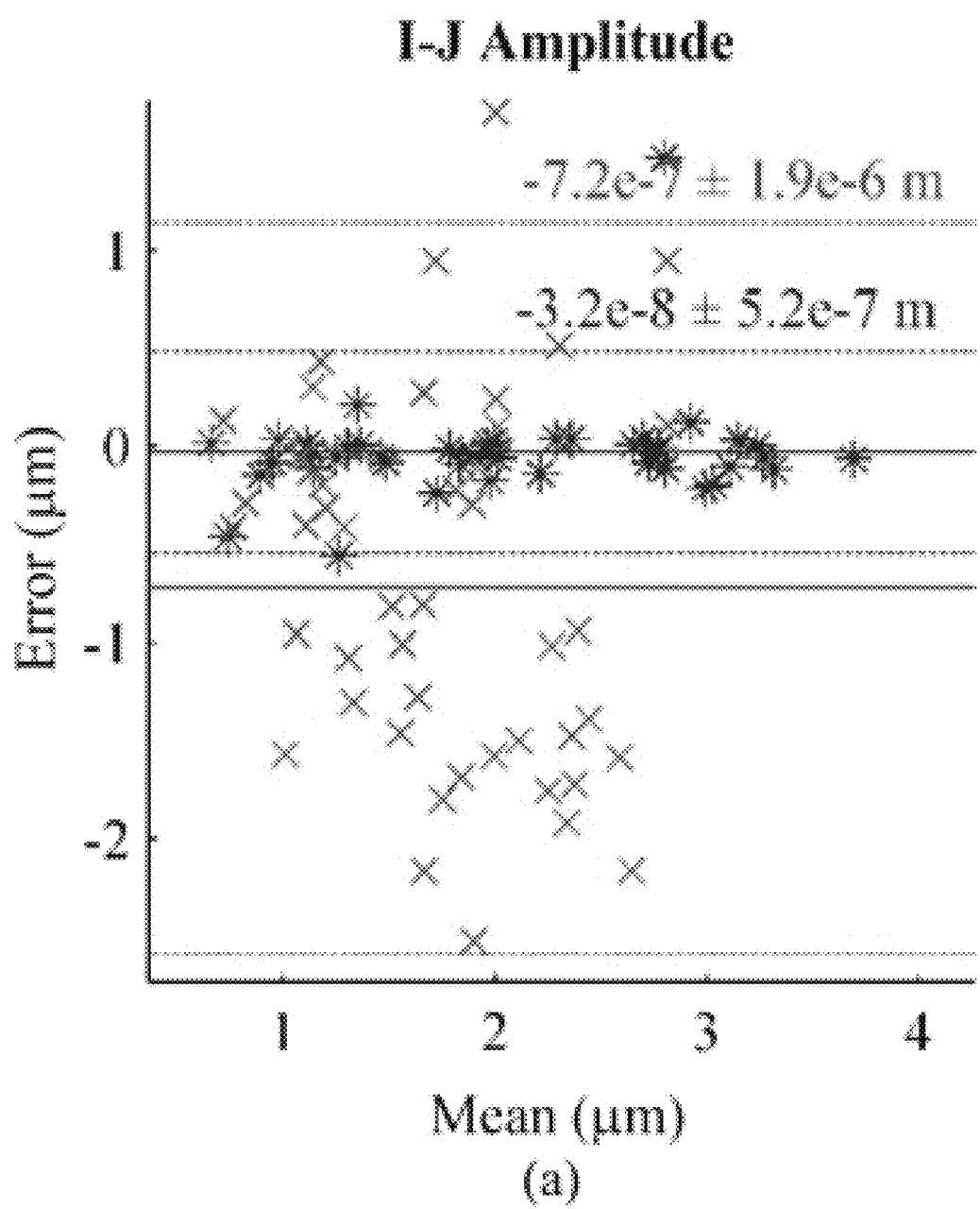
FIG. 14 is a Bland-Altman plot comparing the calibrated (stars) and uncalibrated (x's) methods for I-J amplitude. The calibrated reconstructions had a much smaller standard deviation than the uncalibrated counterparts.
Figure 15:
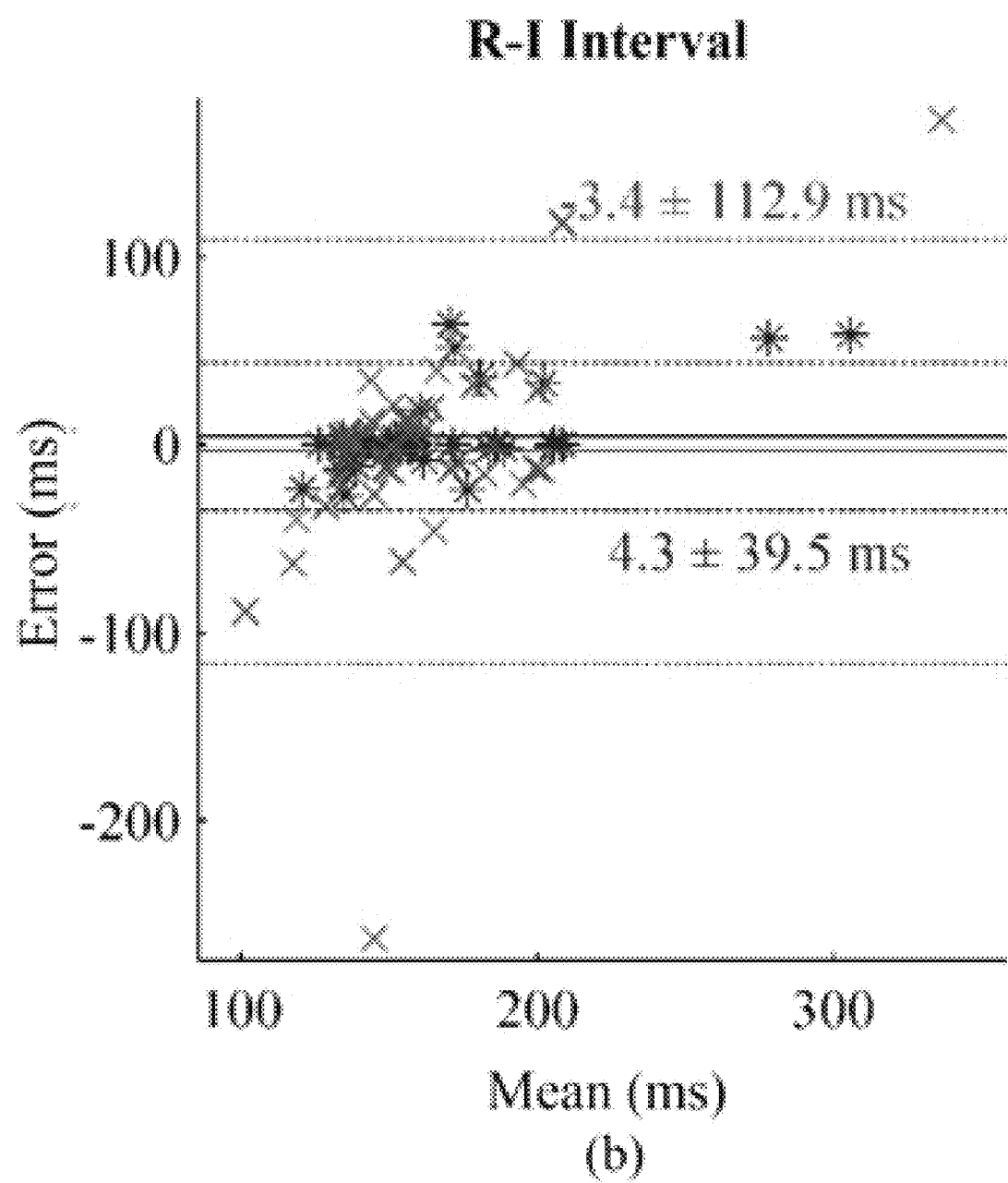
FIG. 15 is a Bland-Altman plot comparing the calibrated (stars) and uncalibrated (x's) methods for R-I amplitude. The calibrated reconstructions had a much smaller standard deviation than the uncalibrated counterparts.
Figure 16:
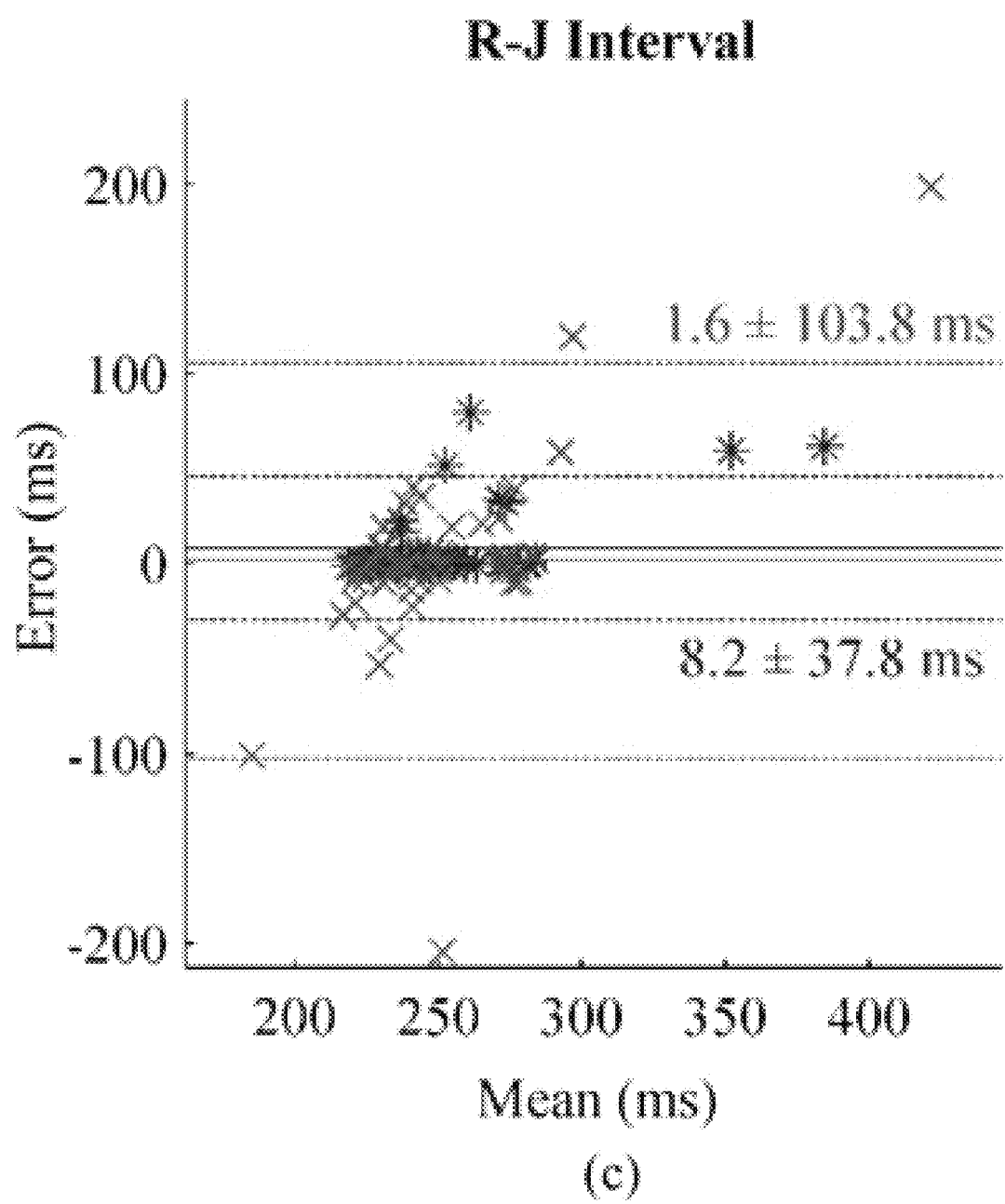
FIG. 16 is a Bland-Altman plot comparing the calibrated (stars) and uncalibrated (x's) methods for R-J amplitude. The calibrated reconstructions had a much smaller standard deviation than the uncalibrated counterparts.
Figure 17:
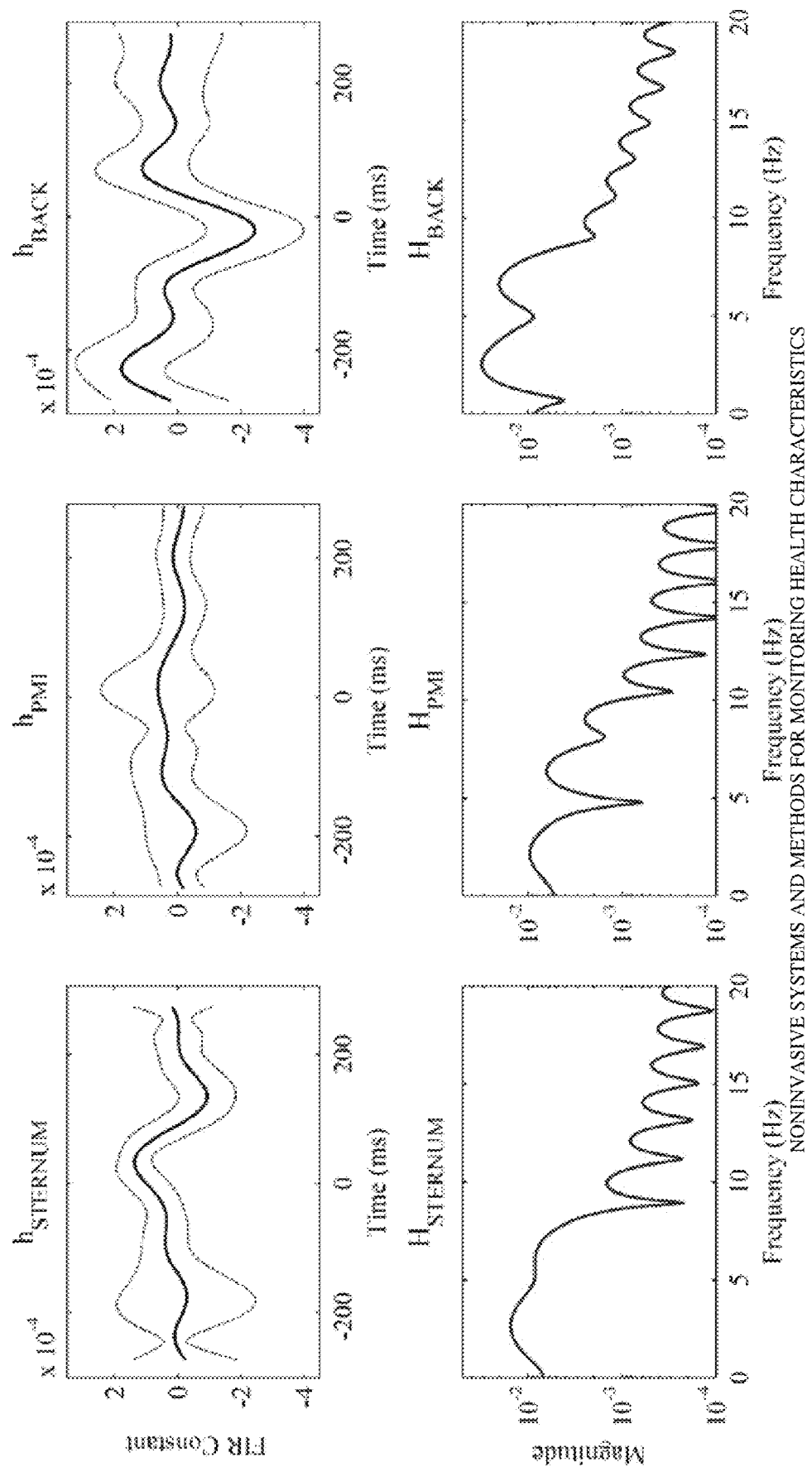
FIG. 17 presents average finite impulse responses of H and their frequency characteristics from each wearable location on the body for all subjects (solid) are shown with the corresponding sample-by-sample standard deviations (dashed). The morphology of the H impulse responses were most consistent between subjects when the wearable accelerometer was worn at the lower back. The impulse responses also are clearly non-causal: significant energy exists in the impulse responses for negative and positive time, and therefore, every sample of $BCG_{WS}$ depends on both past and future samples of $BCG_{WEAR}$.

FIG. 13 shows the waveforms of an example reconstruction from the lower back. The uncalibrated reconstruction in this example appears qualitatively worse than the calibrated, or trained, reconstruction. This observation is supported by the Bland-Altman plots in FIGS. 14-16, which compare the accuracy of the two methods in measuring I-J amplitude, R-I interval, and R-J interval of the WS BCG for all subjects. Specifically, the standard deviation of the uncalibrated measurements is much larger than the calibrated ones. Since the uncalibrated results are worse in all three metrics, calibration is clearly needed to obtain the most accurate results. This suggests that there may be large differences in the true impulse response H between different locations on the same subject and between different subjects at the same location. This is supported by examination of the impulse responses produced by the system identification technique. The average impulse responses from each location on the body, as shown in FIG. 17, revealed high intersubject variability, and the morphology of the FIR filters between subjects were most similar at the lower back. This could be part of the reason why the lower back appears to be the best location to measure the wearable BCG; further work is needed to gain a better understanding of H, $H_{WEAR}$, and $H_{WS}$.

Results for Multiday Trials

Figure 18:
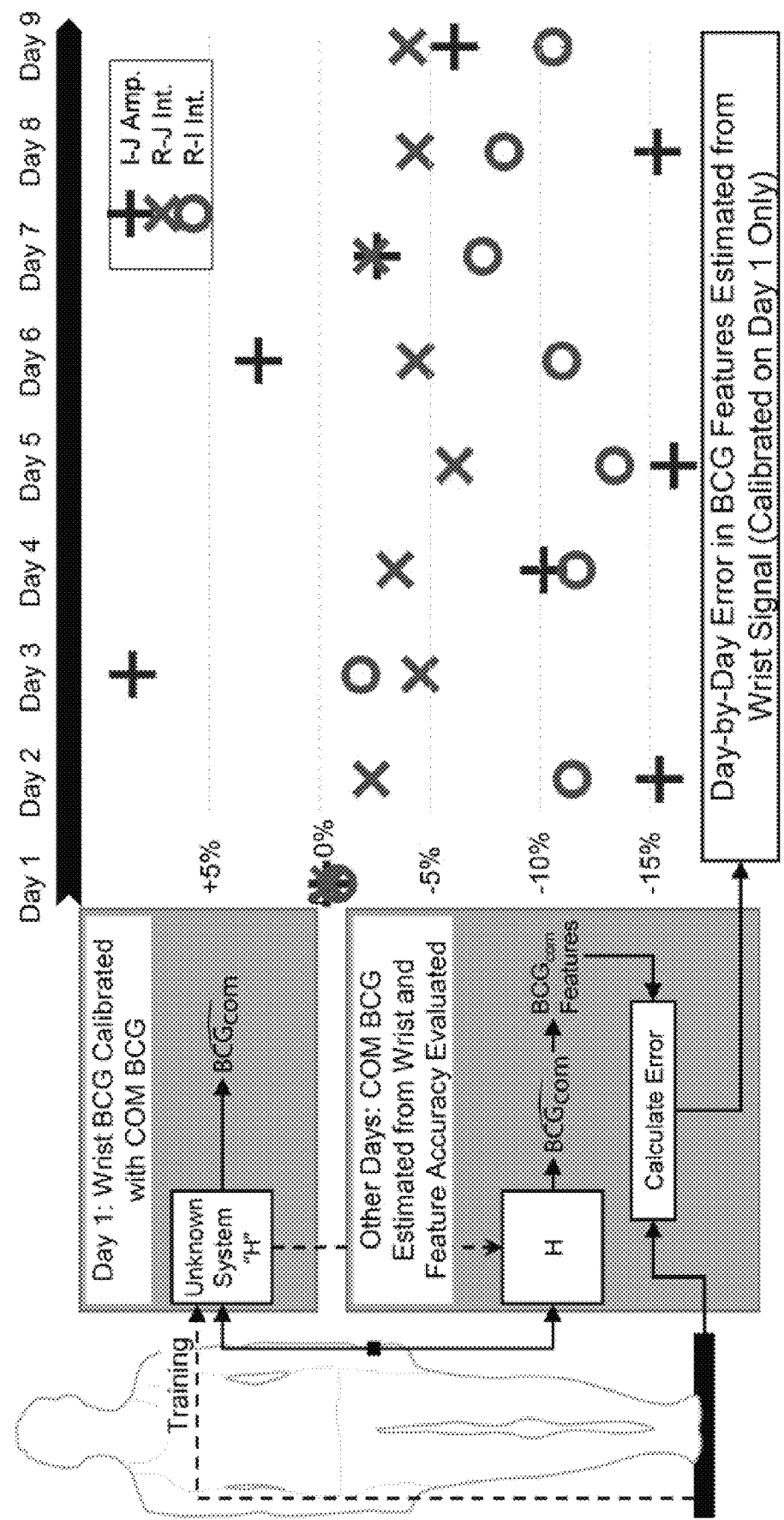
FIG. 18 presents error metrics for reconstructing the WS BCG from the wearable BCG measured at the wrist. The algorithm was trained on the first day, and that calibration was used for each subsequent day. The R-J interval reconstruction provided the lowest error of the three key features.

The error metrics over all nine days of the multiday trials appear in FIG. 18. The I-J amplitude error spanned −16.2% to +8.4%, the R-I interval error was between −13.5% and −0.9%, and the R-J interval error was between −6.2% and −0.5%. As these errors were relatively low and did not trend in any particular direction with time, the wearable BCG is likely most consistent within the same subject and location on the body. It may, therefore, be possible to measure cardiac changes over time with the wearable BCG at one location—such as with accelerometers embedded in a smart watch—using one initial calibration with the scale.

DISCUSSION

In this embodiment, for the first time, a method for estimating the WS BCG with an accelerometer placed on the surface of the skin and a simultaneously acquired ECG is presented. Preliminary validation for this new technique was performed on data from fifteen consenting human subjects. Whereas it has been shown that the acceleration on the surface of the skin differs substantially from whole-body displacement measurements taken with WS BCG platform, training this algorithm with a WS BCG recording from a modified weighing scale allowed accurate re-constructions of the WS BCG from three arbitrary locations on the body for fifteen subjects at rest. (And from the wrist on one subject at rest over several days.)

The lowest error was obtained in reconstructions from the lower back; this was supported by cross validation as well as examination of the FIR filters revealing that the lower back filter had the lowest intersubject variability. This technique could, therefore, enable trending cardiac output and contractility with a wearable device using published BCG analysis tools via a calibration step.

This is also the first demonstration of central hemodynamic measurement from the wrist. Because the BCG signal arises from central hemodynamic forces, the ability to measure the signal from a distal location, such as the wrist, potentially has profound applicability to the important problem of cuffless blood pressure measurement. By pairing wearable BCG measurement from the wrist with additional local pulse measurement modalities—such as photoplethysmography—further inventive pulse-transit time-based approaches for blood pressure monitoring in a smart watch form factor can be made.

Further studies are also needed to validate this technique for subjects whose cardiovascular systems are modulated or diseased since this study included only healthy subjects in quiescence. Freedom to measure the BCG beyond large appliances and the ability to place the wearable sensor on arbitrary places on the body would open up many opportunities for heart monitoring throughout the day, and the present invention serves as a framework for enabling new BCG modalities and applications.

III. Accelerometer Body Sensor Network Improves Systolic Time Interval Assessment with Wearable Ballistocardiography

INTRODUCTION

The three primary STI are PEP, left ventricular ejection time (LVET), and total electromechanical systole ($QS_2$). Since cardiac relaxation and contraction are controlled by intracellular calcium ion recycling, the timing of PEP, LVET, and $QS_2$ are directly related to cardiac cell health. Furthermore, the health of the left ventricle, as the pump for the body's entire circulation, is particularly important to the management of CVD, which affects more than 26 million Americans. During the cardiac cycle, the left ventricle undergoes diastolic filling and systolic ejection in an alternating fashion. The latter phase, systolic ejection, is preceded by the PEP, or the delay from ventricular depolarization to the opening of the aortic valve.

Since PEP (i) is an important metric for heart failure related to cardiac contractility, (ii) is needed for beat-by-beat noninvasive cuff-less blood pressure measurement via arterial pulse transit time, and (iii) has been shown to correlate well ($r^2$=0.86) with the location of the J-wave in the WS BCG, in another exemplary embodiment of the present invention, systems and methods to improve PEP estimation from wearable BCG signals measured with accelerometers worn on the body using an innovative double-integration technique (to estimate sensor displacement from acceleration) and linear models fitted from two features extracted from the BCG signals—namely, the R-J and R-I intervals, or the intervals from the R-wave of an ECG to the J- and I-waves of the BCG. A network of four BCG accelerometers worn on the body and a weighing scale BCG were measured simultaneously and combined with a beat-by-beat cross-validation approach to study the impact of double-integration on PEP accuracy and whether increasing the number of sensors can improve the linear models from R-J and R-I intervals to PEP without over-fitting the training data.

Methods

Experiment

Figure 19:
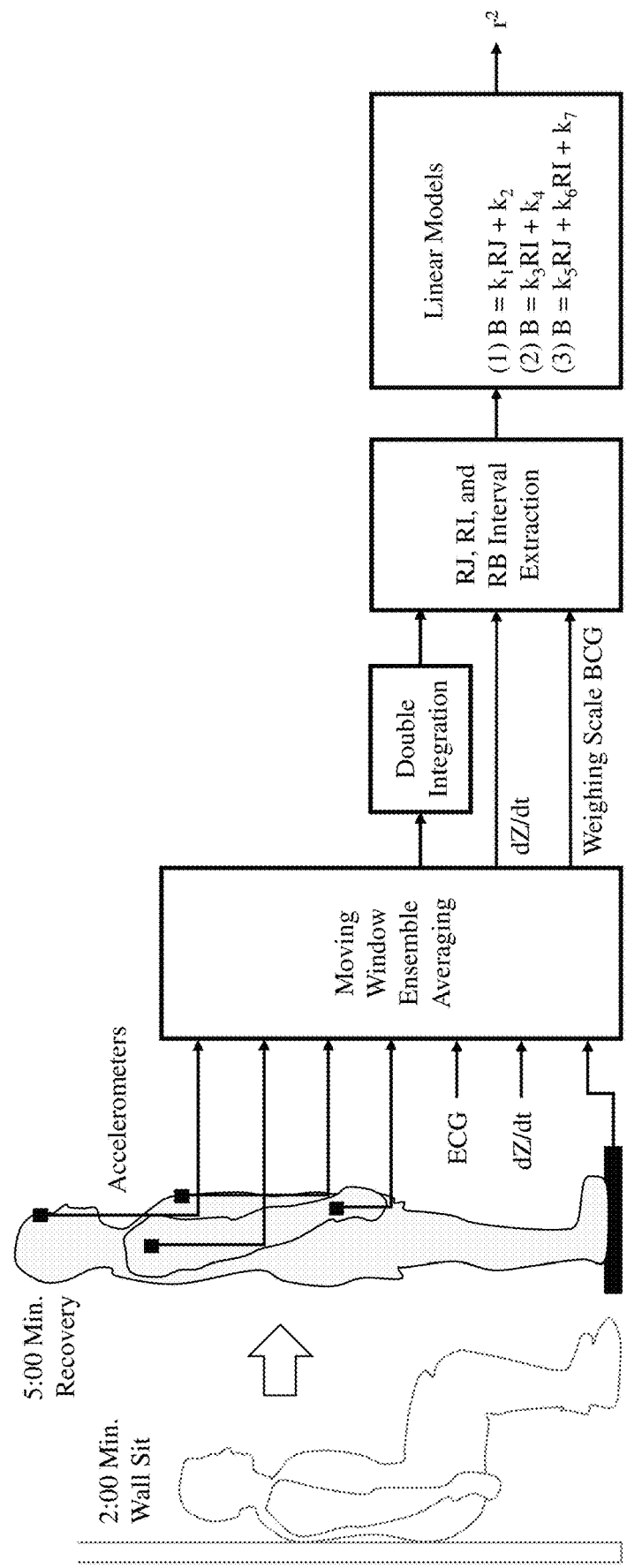
FIG. 19 shows a wearable BCG body sensor network. A subject performed a two minute wall sit to modulate PEP followed by a five minute recording during exercise recovery during which PEP returned to normal. Moving window ensemble averaging was employed to increase signal-to-noise ratio (SNR) ratio, and double-integration was performed to approximate sensor displacement.
Figure 21:
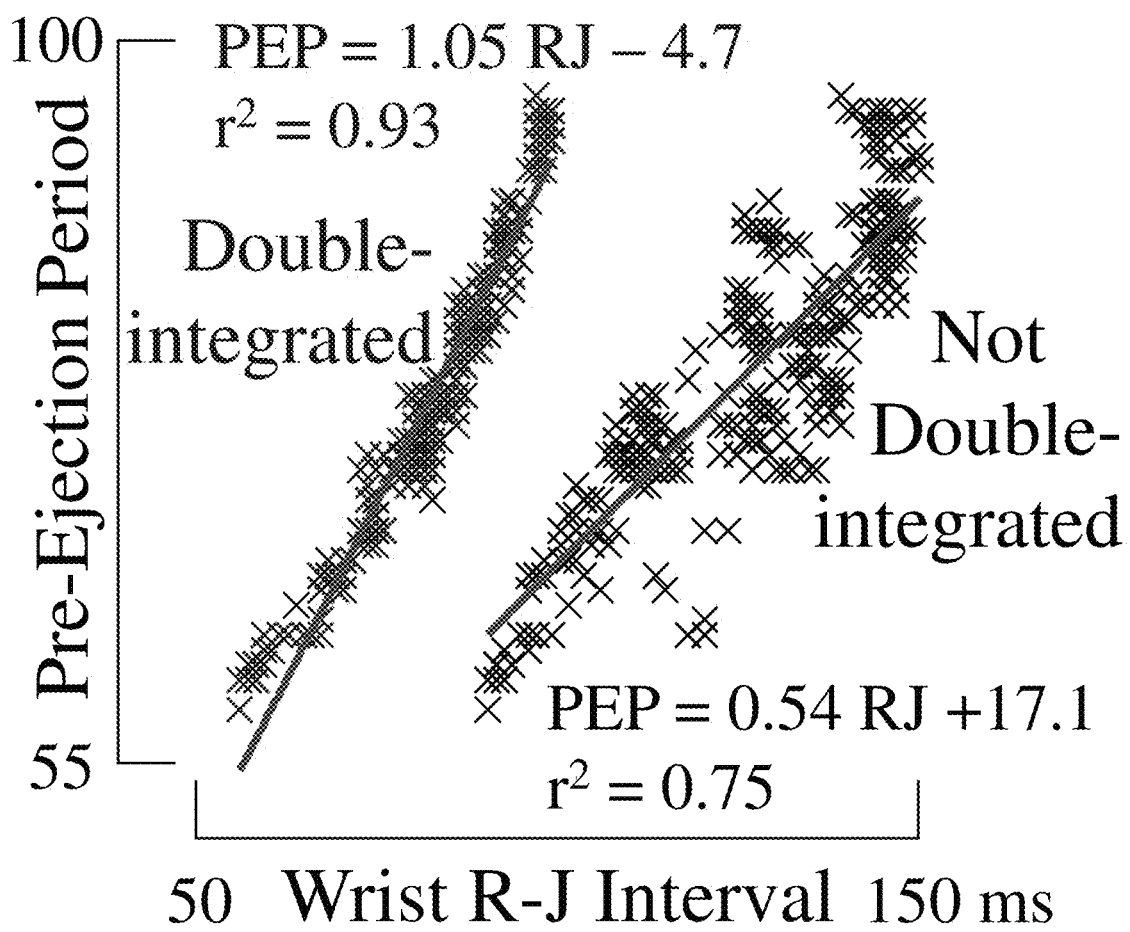
FIG. 21 is a graph illustrating the relationship between PEP and R-J interval for one wearable BCG sensor on one subject. Double integration improved the correlation.
Figure 22:
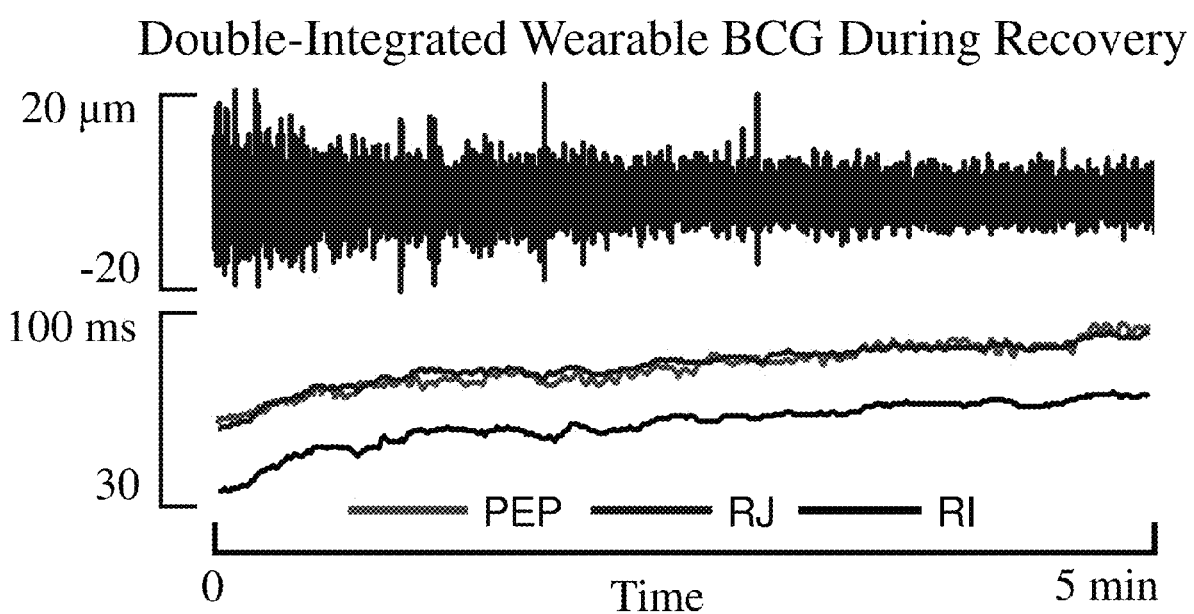
FIG. 22 shows BCG amplitude decreased and PEP, R-J, and R-I intervals increased during exercise recovery.

Four human subjects volunteered for the pilot study (three male and one female, 23±1 years, 177±11 cm, 72±11 kg, 109±5 mmHg SBP, 74±1 mmHg DBP), which was approved by the GT IRB. Each subject was asked to perform an isometric lower-body exercise (i.e., a wall sit) for approximately two minutes as shown in FIG. 19, and the signals were recorded for five minutes immediately following the exercise. This exercise recovery period modulated PEP from 60 to 100 ms as shown in FIG. 21 and FIG. 22.

An ECG configured for a modified Lead II measurement (BN-EL50 wireless ECG, BIOPAC Systems, Inc., Goleta, Calif.), an impedance cardiogram (NICO100C wireless ICG, BIOPAC Systems, Inc.), four instrumentation accelerometers (BCG; 3×356A32, PCB Piezotronics, Depew, N.Y. and 1×5958-A, Brüel & Kjer, Naeurum, Denmark), and a custom weighing scale BCG were sampled simultaneously at $f_s$=1000 Hz with a data acquisition unit (MP150, BIOPAC Systems, Inc.). These accelerometers were chosen for their low noise properties, and details about the WS BCG platform are discussed above. The three PCB Piezotronics accelerometers were attached to each subject's right wrist and right upper arm with kinesiology tape (Kinesio Tex, Kinesio, Albuquerque, N. Mex.) and to the forehead with a headband. The B&K accelerometer was attached to the sternum with a tight elastic band around the thorax. A single axis in the foot-to-head direction was recorded from each wearable sensor.

Signal Conditioning

The signals were processed offline in MATLAB (MathWorks, Natick, Mass.) using an innovative double-integration technique and several widely-accepted methods for analyzing BCG, ICG, and ECG waveforms. First, the signals were bandpass-filtered using Kaiser-window FIR filters (ECG: 3-50 Hz, WS BCG: 3-15 Hz, BCG: 3-50 Hz, dZ/dt: 1-50 Hz). Next, each signal, other than the ECG signal, was segmented into heartbeats using the ECG R-wave as the fiducial where 300 ms before the R-wave and 600 ms after the R-wave were included from each heartbeat. Then, to improve the SNR of each BCG and the ICG dZ/dt signal ($ICG_D$), 9-beat moving window ensemble averages (MEA) were computed where 4 beats before and after each beat were averaged together with the current beat as shown in Equations 12 and 13 where i is the index of the current heartbeat, j is the index of the current sample within the heartbeat, the j index of the location of the ECG R-wave is defined as zero, and n is the BCG sensor index.

$$BCG_{MEA}[n, i, j] = \frac{1}{9}\sum_{k=-4}^{4} BCG[n, i+k, j] \quad (12)$$

$$ICG_{D_{MEA}}[i, j] = \frac{1}{9}\sum_{k=-4}^{4} ICG_D[i+k, j] \quad (13)$$

BCG J-Wave and I-Wave Feature Extraction

Figure 20:
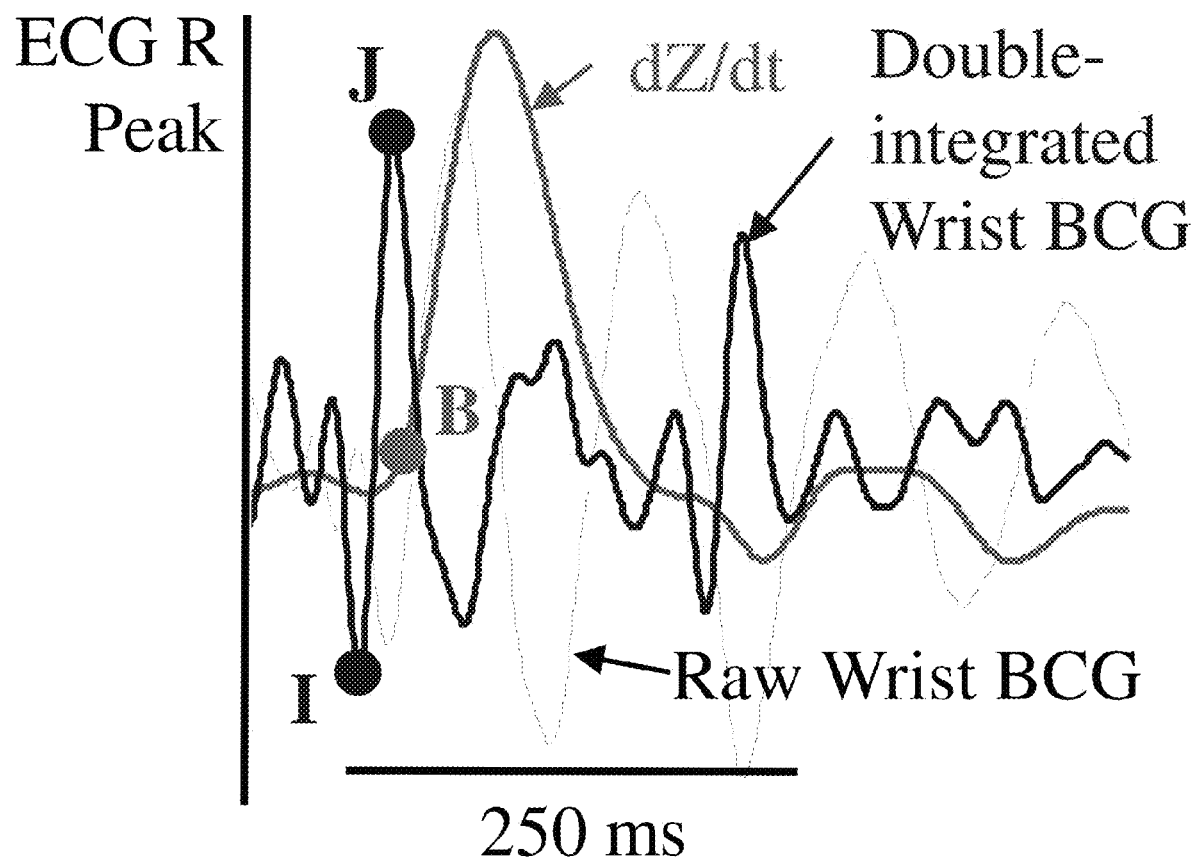
FIG. 20 is a graph of R-J and R-I intervals extracted from the BCG with peak detection, the ICG B-point was determined using an algorithm, and R-B was the PEP ground truth.

Features were extracted from each MEA as shown in FIG. 20. The index of the BCG maximum point within 250 ms after the ECG R-wave was labeled the J-wave and used to determine the beat-by-beat R-J intervals as shown in Equation 14. Similarly, the minimum point between the ECG R-wave and the BCG J-wave was labeled as the I-wave and used to determine the R-I intervals as shown in Equation 15.

$$RJ[n, i] = \operatorname*{argmax}_{0<j<0.25f_s} BCG_{MEA}[n, i, j] \quad (14)$$

$$RI[n, i] = \operatorname*{argmin}_{0<j<RJ_{n,i}} BCG_{MEA}[n, i, j] \quad (15)$$

PEP Ground Truth: ICG B-Point Detection

The time interval from the R-wave of the ECG to the B-point of the impedance cardiogram, or R-B interval, is a widely-accepted measure of PEP and was thus used as the PEP ground truth. In this experiment, the ICG dZ/dt signal ($ICG_D$) was available directly from the BIOPAC analog hardware and did not have to be computed. The B-point in each ICG beat was then determined using a slightly modified version of the second derivative method. Namely, min-crossings were used to find the intercept points of the dZ/dt tangent lines instead of zero-crossings as described below.

First, each beat of the moving ensemble averaged $ICG_D$ was differentiated into $ICG_{DD}$ by subtracting adjacent samples as shown in Equation 16. $ICG_{DD}$ was then low-pass filtered (IIR, $2^{nd}$ order, $f_c$=10 Hz), and the index I and value m of the maximum of $ICG_{DD}$ in the first 250 ms past the ECG R-wave were determined as shown in Equations 17 and 18. Thus, m was the maximum slope achieved in dZ/dt during this period, and I was the location where this slope was achieved. Next, the minimum value p of $ICG_D$ between the ECG R-wave and I was found as shown in Equation 19. Finally, the B-point was determined using the point-slope formula as in Equation 20.

$$ICG_{DD}[i, j] = ICG_{D_{MEA}}[i, j+1] - ICG_{D_{MEA}}[i, j] \quad (16)$$

$$m[i] = \max_{0<j<0.25f_s} ICG_{DD}[i, j] \quad (17)$$

$$l[i] = \operatorname*{argmax}_{0<j<0.25f_s} ICG_{DD}[i, j] \quad (18)$$

$$p[i] = \min_{0<j<l[n,i]} ICG_{D_{MEA}}[i, j] \quad (19)$$

$$PEP[i] = B[i] = \frac{p[i] - ICG_{D_{MEA}}[i, l[i]]}{m[i]} + l[i] \quad (20)$$

Linear Models

Three linear models were fit from beat-by-beat R-J and R-I intervals to PEP as shown in FIG. 21 using robust fitting (bisquare weighting function). PEP was thus modeled as linear combinations of the R-J interval, R-I interval, or both with a constant as shown in Equations 21-23. N is the number of BCG sensors included in the model and PEP, $R-J_n$, and $R-I_n$ are vectors of the PEP, R-J, and R-I intervals from ICG and BCG sensor n, respectively, of one subject's exercise recovery.

$$PEP = \sum_{n=1}^{N} a_n RJ_n + b_n \quad (21)$$

$$PEP = \sum_{n=1}^{N} a_n RI_n + b_n \quad (22)$$

$$PEP = \sum_{n=1}^{N} a_n RJ_n + b_n RI_n + c_n \quad (23)$$

These models were fit to the R-J and R-I intervals from one, two, three, and four sensors in succession to determine the impact of adding information from additional sensors on the body, and the results were compared to those for the weighing scale BCG to evaluate performance. $R^2$ (adjusted) correlation coefficients were then determined.

5×2-Fold Cross Validation

Increasing the number of features in a model often has the unwanted side-effect of over-fitting the training data. To detect this condition, and to determine the optimal filter length in a separate run, 5×2-fold cross validation was used. First, the heartbeats of each subject's recording were randomly labeled 1 or 2 in equal proportions and split into two bins. Within each bin, the MEA for each signal was calculated. Linear models were then fit to features extracted in one bin, and the RMSE of the PEP predictions for the other bin was determined. This was repeated five times for each subject, and the RMSEs from the two folds and five trials were averaged together for an overall average RMSE.

Estimating Sensor Displacement Via Double Integration

Figure 23:
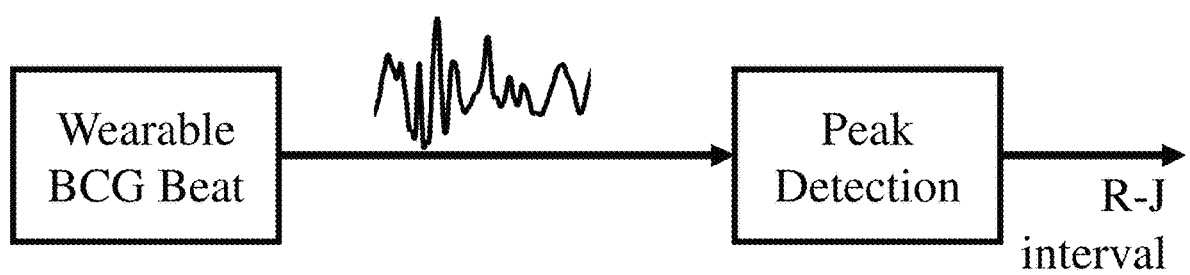
FIG. 23 shows a conventional method for estimating BCG parameters does not correct for differences between sensor types, e.g. displacement vs. acceleration sensors.
Figure 24:
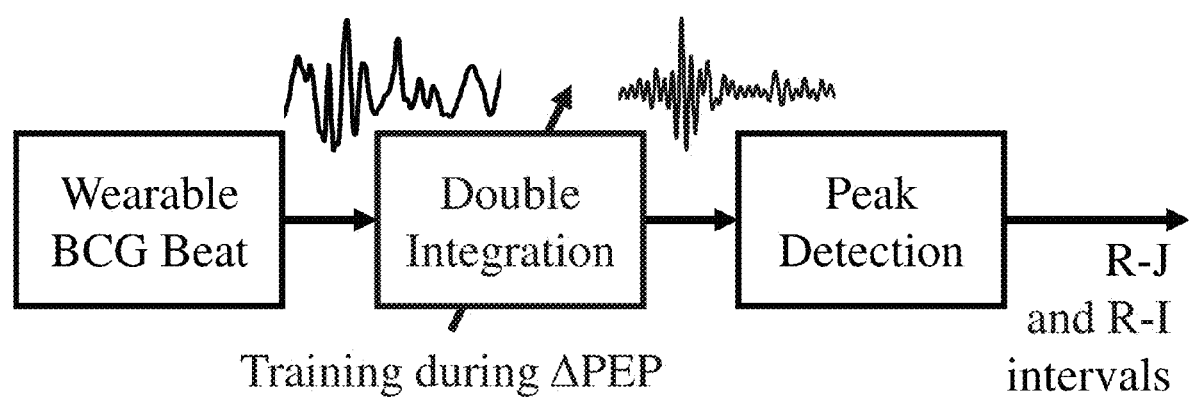
FIG. 24 illustrates an exemplary method according to the present invention that approximates the double integral of the accelerometer waveform to estimate the sensor's displacement.

Currently, feature extraction from wearable BCG sensors (accelerometers) is typically performed as shown in FIG. 23. Wearable BCG sensors are treated as any other BCG measurement, where the I- J- and K-waves are identified using peak detection algorithms. This approach produces low-quality results, and thus a new method was developed as shown in FIG. 24. In this design, wearable BCG measurements are improved by estimating the sensor's displacement (double integral) with an innovative filter consisting of two integrators in-line with high-pass filters (HPF) in the form of moving-average subtractors.

The high-pass cutoff frequency and filter characteristics of moving-average subtraction are determined by a single scalar—the length of the moving average—which can be optimized by sampling the search space with cross validation. In previous studies, the best length for the entire subject population was used. In this experiment, the length was optimized for each BCG using the waveforms of each individual sensor.

Figure 25:
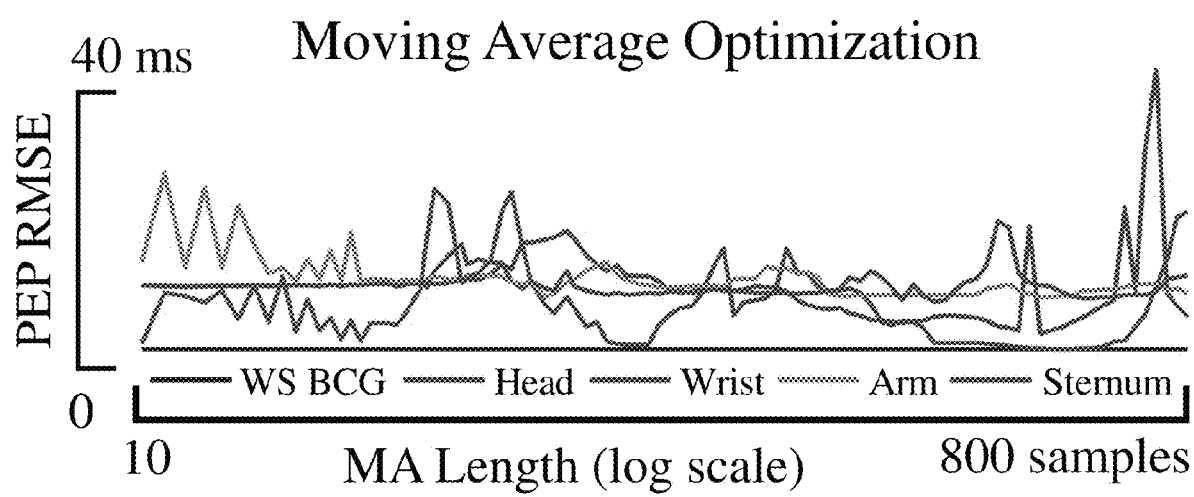
FIG. 25 illustrates that the optimal moving average length varies with sensor location and subject.

After optimizing the moving average for each sensor by computing the average RMSE from cross validation for 100 moving average lengths from 10 to 800 samples as shown in FIG. 25, the optimal moving average length varied greatly from sensor to sensor. The range of moving average lengths—in samples—for each body location were 36 to 534 (forehead), 49 to 467 (wrist), 36 to 489 (upper arm), and 10 to 87 (sternum). Furthermore, sensors placed on different locations on the body on the same subject also had different optimal lengths. Thus, until a better understanding of the mechanical coupling of the wearable sensors to the body is achieved, wearable BCG sensors must be calibrated before accurate results can be obtained.

Results and Discussion

As a result of cross-validation, it is found that the best results without over-fitting the training data were achieved by increasing the number of sensors and including both R-J and R-I intervals in the model. Specifically, both increasing the number of sensors and increasing the number of BCG features from one (R-J interval) to two (R-J and R-I intervals) reduced the average RMSE across all subjects from 6.25 ms to 2.51 ms and reduced the standard deviation of the RMSE between the four subjects from 3.2 ms to 0.8 ms.

This was better than the RMSE for the weighing scale, which was 3.5±2 ms from both R-J and R-I intervals and 4.8±3 ms from R-J intervals alone. Surprisingly, the standard deviation of PEP prediction from the R-J interval was much larger than from the R-I interval, suggesting that the R-I interval may provide better results than the standard R-J method. However, when R-J and R-I timings were combined in one linear model, the results were better than each measurement alone and did not over-fit the training data. This suggests that the R-J and R-I intervals may each bring additional information to the model that improves the estimate.

Figure 26:
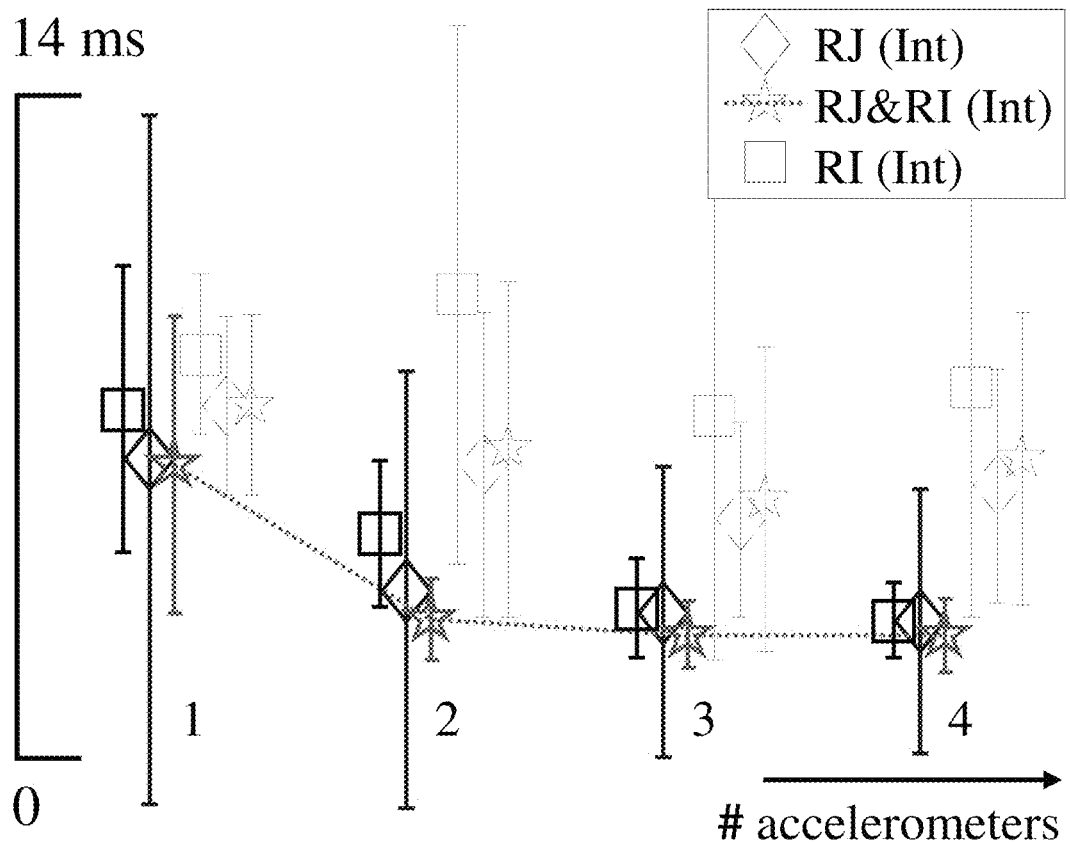
FIG. 26 illustrates increasing the number of accelerometers in the BCG body sensor network, increasing the number of features from one to two, and applying the inventive double-integration filter all reduced the RMSE average and standard deviation during cross validation. Trials without integration are shown in lighter shade.

Furthermore, as shown in FIG. 26, it was found that using a single moving average length for the double-integration filter for all sensors increased the RMSE such that the results were far worse than the current method without filtering. However, when the high-pass filters were optimized for each sensor, both the mean and standard deviation were reduced significantly, particularly when using multiple sensors. This further suggests the need for double integration.

The adjusted $r^2$ linear correlation between weighing scale BCG and PEP was 0.84±0.1 for R-J intervals, 0.87±0.9 for R-I intervals, and 0.89±0.08 for R-J and R-I intervals together. Likewise, the mean and standard deviation of adjusted $r^2$ combining the four accelerometers in the body sensor network with optimized double integration was 0.95±0.008 for R-J intervals, 0.95±0.01 for R-I intervals, and 0.96±0.01 for R-J and R-I intervals together compared to 0.60±0.4, 0.40±0.4, and 0.68±0.3, respectively, for a single wearable BCG sensor.

Thus, while a single sensor performed much worse than the weighing scale BCG, a network of four sensors outperformed the weighing scale. Since the moving ensemble average of nine adjacent beats greatly increased the SNR, this difference likely is mostly due to additional information that multiple sensors provide about the movement of the entire body rather than suppression of motion artifacts.

Wearable BCG can potentially offer the least obtrusive solution for continuous STI monitoring in activities of daily living. A wearable BCG sensing system can be attached to a subject in a smart watch (wrist), headband (forehead), chest strap (sternum), or smart phone armband (arm) form factor with the use of a low noise accelerometer rigidly attached to the body.

Additionally, using wearable sensors together with a weighing scale-based BCG may provide the best results since the wearable can be calibrated by the scale. The wearable sensors could then provide regular measurements of STI and other parameters throughout normal activities of daily living. Further investigation into the influence of sensor positioning on signal quality and interpretation is warranted. The ability to measure central cardiac time intervals from distal locations on the body is an exciting capability that wearable BCG appears to provide. Measurements of central cardiac events from devices worn on the periphery could enable a host of new modalities such as cuff-less blood pressure from pulse-transit time and beat-by-beat wearable hemodynamics assessment in harsh environments such as underwater and space.

Numerous characteristics and advantages have been set forth in the foregoing description, together with details of structure and function. While the invention has been disclosed in several forms, it will be apparent to those skilled in the art that many modifications, additions, and deletions, especially in matters of shape, size, and arrangement of parts, can be made therein without departing from the spirit and scope of the invention and its equivalents as set forth in the following claims. Therefore, other modifications or embodiments as may be suggested by the teachings herein are particularly reserved as they fall within the breadth and scope of the claims here appended.

What is claimed is:

1. A system for providing ballistocardiogram (BCG) data from a user comprising:
    a wearable sensor configured to detect, from the user, cardiogenic surface vibration waveforms;
    a calibrating sensor configured to detect, from the user, cardiogenic center-of-mass (COM) vibration waveforms; and
    a processor configured to:
        determine a modification factor for the surface vibration waveforms based on the COM vibration waveforms;
        generate calculated fixed BCG data based at least in part on subsequent cardiogenic surface vibration waveforms and the modification factor, the subsequent cardiogenic surface vibration waveforms being received from the wearable sensor while the calibrating sensor is not in contact with the user; and
        generate at least one health-related output based on the calculated fixed BCG data.

2. The system of claim 1, wherein the wearable sensor comprises a wearable wrist sensor.

3. The system of claim 1, wherein the wearable sensor comprises a wearable chest sensor.

4. The system of claim 1, wherein the wearable sensor comprises an elastic band fittable for the user's arm.

5. The system of claim 1, wherein the wearable sensor comprises an elastic band fittable for the user's chest.

6. The system of claim 1, wherein the wearable sensor comprises an adhesive patch.

7. The system of claim 1, wherein the wearable sensor comprises an adhesive patch configured for adhesive attachment to the user's skin.

8. The system of claim 1, wherein the calibrating sensor comprises a weighing scale configured to measure BCG signals.

9. The system of claim 1, wherein the calibrating sensor comprises a chair sensor for chair configured to measure BCG signals.

10. The system of claim 1, wherein the calibrating sensor comprises a bed sensor to measure BCG signals.

11. The system of claim 1, wherein the at least one health-related output comprises a condition of the user's heart.

12. The system of claim 1, wherein the at least one health-related output comprises systolic time interval measurements.

13. The system of claim 1, wherein the at least one health-related output comprises cardiac output.

14. The system of claim 1, wherein the at least one health-related output comprises changes in cardiac output.

15. The system of claim 1, wherein the processor is configured to run an algorithm for modifying the surface vibration waveforms using a regularized least squares based system identification method using the COM vibration waveforms as calibration waveforms to modify the surface vibration waveforms.

16. The system of claim 1, wherein the processor is configured to run an algorithm for modifying the surface vibration waveforms using adaptive signal estimation and the calibrating sensor waveform as the desired response.

17. The system of claim 1 further comprising:
an electrocardiogram (ECG) sensor configured to receive, from the user, ECG data;
wherein the processor is configured to estimate a weighing scale ballistocardiogram (WS BCG) from data from the wearable sensor, the calibrating sensor, and the ECG sensor.

18. A system for providing ballistocardiogram (BCG) data from a user comprising:
a wearable sensor configured to detect, from the user, cardiogenic surface vibration waveforms;
a calibrating sensor configured to detect, from the user, cardiogenic center-of-mass (COM) vibration waveforms; and
a processor configured to:
determine a modification factor for the surface vibration waveforms based on the COM vibration waveforms; and
generate calculated fixed BCG data based at least in part on subsequent cardiogenic surface vibration waveforms and the modification factor, the subsequent cardiogenic surface vibration waveforms being received from the wearable sensor while the calibrating sensor is not in contact with the user; and
generate at least one health-related output based on the calculated fixed BCG data;
wherein the wearable sensor is in a form selected from the group consisting of a wearable chest sensor, an adhesive patch, and an adhesive patch configured for adhesive attachment to the user's skin;
wherein the calibrating sensor is in a form of a weighing scale configured to measure BCG signals; and
wherein the health-related output is selected from the group consisting of a condition of the user's heart, systolic time interval measurements, cardiac output, and changes in cardiac output.

19. The system of claim 18, wherein the processor is configured to run an algorithm for modifying the surface vibration waveforms using a regularized least squares based system identification method using the COM vibration waveforms as calibration waveforms to modify the surface vibration waveforms.

20. The system of claim 18, wherein the processor is configured to run an algorithm for modifying the surface vibration waveforms using adaptive signal estimation and the calibrating sensor waveform as the desired response.

* * * * *